(12) United States Patent
Hossack et al.

(10) Patent No.: US 12,016,588 B2
(45) Date of Patent: Jun. 25, 2024

(54) SURGICAL INCISION APPARATUS AND RELATED METHODS THEREOF

(71) Applicant: University of Virginia Patent Foundation, Charlottesville, VA (US)

(72) Inventors: John A. Hossack, Charlottesville, VA (US); Nishaki Mehta, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 395 days.

(21) Appl. No.: 17/046,428

(22) PCT Filed: Apr. 10, 2019

(86) PCT No.: PCT/US2019/026750
§ 371 (c)(1),
(2) Date: Oct. 9, 2020

(87) PCT Pub. No.: WO2019/199940
PCT Pub. Date: Oct. 17, 2019

(65) Prior Publication Data
US 2021/0106351 A1    Apr. 15, 2021

Related U.S. Application Data

(60) Provisional application No. 62/655,916, filed on Apr. 11, 2018.

(51) Int. Cl.
*A61B 17/3211* (2006.01)
*A61B 17/00* (2006.01)
*A61B 17/32* (2006.01)

(52) U.S. Cl.
CPC . *A61B 17/3211* (2013.01); *A61B 2017/00876* (2013.01); *A61B 2017/320052* (2013.01); *A61B 2017/32113* (2013.01)

(58) Field of Classification Search
CPC ............ A61B 17/3209; A61B 17/3211; A61B 2017/00876; A61B 2017/22039;
(Continued)

(56) References Cited

U.S. PATENT DOCUMENTS 4,266,549 A    5/1981  Kimura
4,270,416 A    6/1981  Thompson
(Continued)

OTHER PUBLICATIONS

Shane, Thomas, "International Search Report and Written Opinion of the International Searching Authority", International patent application No. PCT/US2019/026750, dated July, 1, 2019, 14 pages.
(Continued)

*Primary Examiner* — Jocelin C Tanner
(74) *Attorney, Agent, or Firm* — Robert J. Decker

(57) ABSTRACT

A surgical incision apparatus and method for puncturing a cutaneous layer of a subject for providing guided access to a subcutaneous organ or subcutaneous cavity (or specified target region) of the subject. The apparatus may include a retention body configured for securing a cutting tool therein and a housing configured for receiving the retention body. The apparatus includes a guidewire holder member configured for receiving a guidewire therein and aligning with the guidewire to allow the cutting tool to travel along the guidewire. The retention body is configured to be movably attached relative to the housing to allow the retention body and cutting tool to advance toward the subject to a deployed position, and subsequently withdraw to a retracted position.

111 Claims, 17 Drawing Sheets

(58) Field of Classification Search
CPC ......... A61B 2017/320052; A61B 2017/32113; A61B 2017/32096; A61B 2017/320708; A61B 2017/320791; A61B 2090/0811
See application file for complete search history.

(56) References Cited

U.S. PATENT DOCUMENTS

| | | | |
|---|---|---|---|
| 4,378,624 A | | 4/1983 | Klingenberg |
| 4,517,973 A | | 5/1985 | Sunago et al. |
| 4,633,860 A | | 1/1987 | Korth et al. |
| 4,655,223 A | | 4/1987 | Kim |
| 4,688,570 A | | 8/1987 | Kramer et al. |
| 4,730,376 A | | 3/1988 | Yamada |
| 5,108,408 A | | 4/1992 | Lally |
| 5,449,068 A | | 9/1995 | Gharibian |
| 5,513,405 A | * | 5/1996 | Bradbury, Jr. ............ B26B 5/00 7/105 |
| 5,649,944 A | | 7/1997 | Collins |
| 5,749,886 A | | 5/1998 | Abidin et al. |
| 5,817,117 A | | 10/1998 | Cartaxo |
| 5,868,250 A | | 2/1999 | Brackett |
| 6,270,501 B1 | | 8/2001 | Freiberg et al. |
| 6,663,616 B1 | | 12/2003 | Roth et al. |
| 7,172,611 B2 | | 2/2007 | Harding et al. |
| 7,341,596 B2 | | 3/2008 | Heppler |
| 8,172,801 B2 | | 5/2012 | Adams |
| 8,512,363 B2 | | 8/2013 | Heppler |
| 8,596,453 B2 | | 12/2013 | Hoftman et al. |
| 8,752,700 B1 | | 7/2014 | Hoftman |
| 8,795,384 B2 | | 8/2014 | Nelson et al. |
| 9,456,840 B1 | | 10/2016 | Huddleston |
| 10,383,655 B2 | * | 8/2019 | Rauchwerger ..... A61B 17/3211 |
| 2004/0133227 A1 | * | 7/2004 | Shang ............... A61B 17/32093 606/182 |
| 2004/0181246 A1 | * | 9/2004 | Heppler ............. A61B 17/3213 606/167 |
| 2006/0111733 A1 | | 5/2006 | Shriver |
| 2010/0036404 A1 | * | 2/2010 | Yi ...................... A61B 17/3215 606/167 |
| 2011/0283542 A1 | * | 11/2011 | Wu ........................ B26B 5/003 30/162 |
| 2012/0226299 A1 | * | 9/2012 | Heppler ............. A61B 17/3211 606/167 |
| 2012/0232571 A1 | | 9/2012 | Muto et al. |
| 2013/0218183 A1 | * | 8/2013 | Rauchwerger ..... A61B 17/3211 606/167 |
| 2015/0289901 A1 | * | 10/2015 | Khan ................. A61B 17/3494 606/182 |
| 2016/0158501 A1 | * | 6/2016 | Farris .................... A61M 29/00 606/167 |

OTHER PUBLICATIONS

Nakamura, Yukari, "International Preliminary Report on Patentability", International patent application No. PCT/US2019/026750, dated Oct. 13, 2020, 1 page.

* cited by examiner

SURGICAL INCISION APPARATUS AND RELATED METHODS THEREOF

RELATED APPLICATIONS

The present application is a national stage filing of International Application No. PCT/US2019/026750, filed Apr. 10, 2019, which claims benefit of priority under 35 U.S.C. § 119 (e) from U.S. Provisional Application Ser. No. 62/655,916, filed Apr. 11, 2018, entitled "Surgical Incision Guide Device and Related Method"; the disclosures of which are hereby incorporated by reference herein in their entirety.

FIELD OF INVENTION

The present disclosure relates generally to a surgical incision apparatus; and more particularly to a wire aligned surgical guide device with magnetic tracking.

BACKGROUND

As the field of surgery has evolved, the desire to utilize minimally invasive techniques has increased. Surgical complications have long represented a substantial source of patient harm, and, in the United States alone, cost an estimated 25 billion dollars annually.

Minimally invasive surgery is becoming increasingly prevalent in the surgical space. A key component of many of these surgeries is vascular access.

The most commonly used procedure to facilitate vascular access is known as the Seldinger technique. In this technique, a needle is inserted into the vessel of choice. Following insertion, a wire is cannulated through the needle and into the vessel. The next step in the process is to remove the needle and introduce a hollow catheter; however, this requires dilation of the entry site with a scalpel.

One of the first steps of the Seldinger technique is dilating the blood vessel is to nick the skin with the scalpel. This simple dilation becomes complicated by bleeding from the initial needle entry, which essentially renders the incision "blind". Due to this, approximately 8% of such incisions result in an unintentional vessel puncture, which requires additional surgery to remedy.

Dilatation of the catheter entry is fraught with errors with the surgeon hurting himself or a nick which is too deep or too far from the access to the needle. There is often a skin bridge between the needle and the incision which renders the incision futile.

There are percutaneous medical devices that function to evacuate air or fluid from body cavities or to obtain vascular access. Still referring to the Seldinger technique, for example, often a superficial dermatotomy, commonly referred to as a "skin-nick," is performed with a surgical scalpel blade immediately adjacent to the entry of the guidewire, to enlarge the entry site. A rigid dilator is often then passed over the guidewire to enlarge the deeper aspects of the tract and allow the subsequent medical device to pass smoothly over the guidewire into the desired cavity or lumen. In spite of the fact that a guidewire leads to the precise place where the skin nick is to be made, the dermatotomy is often performed with a traditional scalpel, employing only limited visual guidance and the free hand of the operator. In addition, back bleeding from the vascular access via the needle can confound visualization of the site. In urgent settings, with poorly positioned patients, in poorly lighted rooms, a precisely placed skin nick can require significant concentration at a time when there are other pressing issues with the patient. In addition, it can pose a possible needle stick injury to the operator and the assistant. Inappropriate dermatotomy can also lead to repeat attempts, skin tear, delayed healing and potentially laceration of the neighboring structures. In addition, inappropriate dermatotomy can result in up to 20-25% catheter related infections. Several vital structures including arteries, veins and nerve bundles often run a few millimeters (mm) superficial to the skin level of entry. The current scalpel blinded dermatotomy does not permit scalpel entry co-axial to the wire and therefore the blade entry might be discordant which could further lead to collateral injury. Additionally, there is a huge impetus to reduce sharp related injury and the scalpel on the surgical field can increase inadvertent risks.

Therefore, there is a long felt need for surgical incision guide device and a wire aligned scalpel guide device and related methods thereof.

SUMMARY OF ASPECTS OF EMBODIMENTS OF THE INVENTION

An aspect of an embodiment provides a cutting tool incision guide whereby the device can be threaded onto the guidewire and routed to the site of the incision of the subject. A single blade (e.g., cutting tool) could be moved forward and backward out of a housing at specific intervals, such as for example, intervals at about 0.25, 0.5, 0.75, and 1 centimeter. These intervals will be refined and adjusted as specified for operational and anatomical demands. Resistant notches (e.g., check structures) in the design would allow for the user to lock or fix the device in place at any of these intervals, allowing for precise incision depth. To minimize any potential for a skin tag between the guide wire and the incision site, an open portal design allows for the cutting tool (e.g., scalpel or blade) to directly contact the guidewire. In addition, the blade can be angled slightly or as specified, making contact with the guidewire at the optimal point for incision.

In an embodiment, a single blade (e.g., cutting tool) could be moved forward and backward out of a housing at specific intervals, such as for example, intervals greater or less than at about 0.25, 0.5, 0.75, and 1 centimeter. For example, the single blade or cutting tool may move forward and backward out of a housing between a range of about 1 to 10 centimeters (and any number of partial degrees of position thereof) to an intended organ, cavity, space or target region of the subject. In an embodiment, the single blade or cutting tool may advance greater than about 10 centimeters to an intended organ, cavity, space, or target region of the subject. In an embodiment, a single blade or cutting tool may move forward and backward less than about 025 centimeters to an intended organ, cavity, space, or target region of the subject.

An aspect of an embodiment of the present invention provides, among other things, a surgical incision apparatus (e.g., housing portion of the like) that completely covers the scalpel blade (or cutting tool) in its entirety when it is not deployed (or in a retracted position). This further reduces the risk of inadvertent injuries from sharps laying on the surgical field.

The present inventor submits that in the context of gaining minimally invasive peripheral access for percutaneous interventions (catheters), there is sometimes a need to expand the access point using a delicate scalpel manipulation. An aspect of an embodiment of the present invention provides, among other things, an apparatus and method to improve safety and efficiency for this procedure.

An aspect of an embodiment of the present invention provides, among other things, surgical incision guide device and related method thereof.

An aspect of an embodiment of the present invention provides, among other things, a wire mounted or aligned scalpel guide device and related method thereof.

An aspect of an embodiment of the present invention provides, among other things, a surgical incision apparatus that effects a wire aligned surgical guide device with magnetic tracking.

Several hundred thousand percutaneous access procedures are conducted annually in the US in the context of introducing various imaging, diagnostic, sampling or therapeutic catheters. Usually, a simple needle puncture is sufficient to provide access from the skin to the blood vessel or the desired body cavity. The next step is to utilize this access via the needle and guidewire to thread larger caliber tubes. Hence graded expansion of this entry is done. This is performed using a manual scalpel procedure where the scalpel is approximated to the entry point of the wire. The present inventor submits that since this procedure is blinded, it poses risk to laceration or tear of the blood vessel or body organs at the point of needle entry or a scalpel incision that is not in plane with the wire. In addition, the present inventor submits that since it is not controlled, there remains a risk of direct injury to the surgeon and to the patient. The present inventor submits that depending on body type and location of access, e.g., groin versus antecubital versus neck (e.g. obese), the procedure can become more complex than in simpler cases not involving excess skin and subcutaneous fat.

An aspect of an embodiment of the present invention provides, among other things, an efficient and elegant guide device that can be railed onto the in-dwelling wire. This provides a track aligned with the wire so that the scalpel (or other cutting tool) can naturally follow an optimal path from the skin surface to the required depth.

In an embodiment of the surgical incision guide device, graded marking will be visible or palpable with tactile feedback (e.g. check structures) to allow the operator to determine depth of entry with the scalpel blade. Moreover, the scalpel blade mounting mechanism can easily engage or disengage the scalpel blade allowing for any blade (or cutting tool) to be mounted based on the surgical need.

An aspect of an embodiment of the present invention provides, among other things, an efficient and elegant guide device that can be railed onto the in-dwelling wire by use of magnetic forces. Magnetic forces from magnets lining the housing body can magnetize the blade (or cutting tool) as it moves from the retracted position to the deployed position. This magnetic force exerted by the "now magnetized" cutting tool provides for tracking and alignment with the guidewire such that cutting tool (e.g. scalpel) can magnetically follow an optimal path from the skin surface to the required depth. This magnetic force exerted by the "now magnetized" cutting tool provides for tracking and alignment with the guidewire such that cutting tool (e.g. scalpel) can magnetically pull the guidewire toward the scalpel and in direct contact with the scalpel.

In an embodiment, placement of the rare earth magnets can magnetize the scalpel (e.g., cutting tool) even if the cutting tool is housed in polymer filling structure, for example.

An aspect of an embodiment of the apparatus provides for enabling a faster, safer and improved scalpel placement (or other medical tool placement) in the context of forming a slightly increased surgical access in the vicinity of a wire previously placed into a patient vessel.

An aspect of an embodiment of the apparatus provides a flange disposed on the retention body and/or housing acting as a dam stop to prevent the blade (or cutting tool) form slipping or sliding too far forward.

An aspect of an embodiment of the apparatus provides the entrance to the guide wire holder that may include a conical guide (like a funnel) to allow for easier guidewire threading. The exit point of the guidewire through the guidewire holder may have an unroofing to allow for magnetized scalpel and the guide wire to track one another without an overlying interface. In an embodiment, the exit point of the guidewire through the guidewire holder may have an unroofing (e.g., exposed) to allow for magnetized scalpel (or the non-magnetized scalpel) and the guide wire to track one another without an overlying interface so as to make direct contact with one another. An aspect of an embodiment of the apparatus may provide a completely self-contained unit thus reducing risk of inadvertent injury.

An aspect of an embodiment of the apparatus may be used multiple times in a single procedure and stored in a sterile container until the specified time and place of use. Alternatively, the apparatus may be single use or disposable.

An aspect of an embodiment of the apparatus may have a housing, retention body, or cutting tool that may be straight or curved, or combination thereof.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/operator/customer/client/server or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

An aspect of an embodiment of the present invention provides, among other things, the following: a surgical incision apparatus for puncturing a cutaneous layer of a subject for providing guided access to a subcutaneous organ or subcutaneous cavity of the subject. The apparatus may comprise: a retention body configured for securing a cutting tool therein, wherein the retention body having a distal end and proximal end; a housing configured for receiving the retention body, wherein the housing having a distal end and proximal end; a guidewire holder member disposed on the housing configured for receiving a guidewire therein and aligning with the guidewire to allow the cutting tool to travel along the guidewire; and wherein the retention body is configured to be movably attached relative to the housing to allow the distal end of the retention body to advance toward the subject to a deployed position.

An aspect of an embodiment of the present invention provides, among other things, the following: a surgical kit that may comprise a cutting tool; and a surgical incision apparatus, which may be used for puncturing a cutaneous layer of a subject for providing guided access to a subcutaneous organ or subcutaneous cavity of the subject. The surgical incision apparatus may comprise: a retention body configured for securing the cutting tool therein, wherein the retention body having a distal end and proximal end; a housing configured for receiving the retention body, wherein the housing having a distal end and proximal end; a guidewire holder member disposed on the housing configured for receiving a guidewire therein and aligning with the guidewire to allow the cutting tool to travel along the guidewire; and wherein the retention body is configured to be movably attached relative to the housing to allow the distal end of the retention body to advance toward the subject to a deployed position. The kit may further comprise a guidewire, other medical instrument, material or device, or the like.

An aspect of an embodiment of the present invention provides, among other things, the following: a surgical method for puncturing a cutaneous layer of a subject for providing guided access to a subcutaneous organ or subcutaneous cavity of the subject. The method may comprise: securing a cutting tool with a retention body; disposing the retention body with a housing; receiving a guidewire on the housing for aligning the housing with the guidewire; and advancing the retention body wherein the cutting tool travels along the guidewire and advances toward the subject to a deployed position to achieve the access to the subcutaneous organ or subcutaneous cavity of the subject. The method may also include magnetically attracting the guidewire (other medical instrument, material or device, or the like) toward the cutting tool while the cutting tool travels along the guidewire. The method may also include magnetically attracting the guidewire toward a magnet disposed on the retention body and/or housing.

An aspect of an embodiment of the present invention provides, among other things, a surgical incision apparatus and method for puncturing a cutaneous layer of a subject for providing guided access to a subcutaneous organ or subcutaneous cavity (or specified target region) of the subject. The apparatus may include a retention body configured for securing a cutting tool therein and a housing configured for receiving the retention body. The apparatus includes a guidewire holder member configured for receiving a guidewire therein and aligning with the guidewire to allow the cutting tool to travel along the guidewire. The retention body is configured to be movably attached relative to the housing to allow the retention body and cutting tool to advance toward the subject to a deployed position (or multiple deployed positions), and subsequently withdraw to a retracted position (or multiple retracted positions).

The invention itself, together with further objects and attendant advantages, will best be understood by reference to the following detailed description, taken in conjunction with the accompanying drawings.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 1:
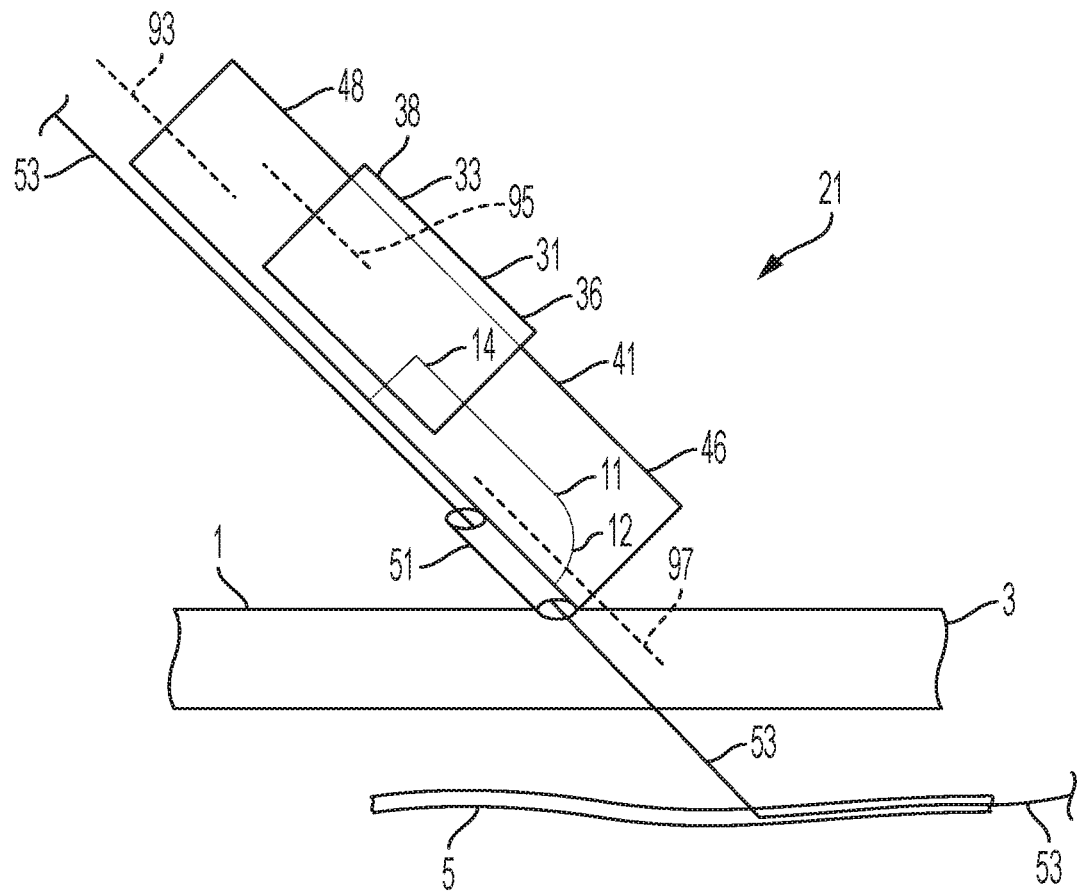
FIG. 1 schematically illustrates an embodiment of the surgical incision apparatus with the retention body and cutting tool in a retracted position in an environment of the subject.

Referring to various aspects of embodiments represented by FIGS. 1-18, a surgical incision apparatus 21 is provided for puncturing a cutaneous layer 3 of a subject 1 for providing guided access to a subcutaneous organ 5 or subcutaneous cavity of the subject 1. The surgical incision apparatus 21 may include a retention body 31 configured for securing a cutting tool 11 therein, wherein the retention body 31 may have a distal end 36 and proximal end 38. The apparatus 21 may include a housing 41 configured for receiving the retention body 31, wherein the housing 41 may have a distal end 46 and proximal end 48. The apparatus 21 may include a guidewire holder member 51 disposed on the housing 41 configured for receiving a guidewire 53 or the like therein and aligning with the guidewire 53 to allow the cutting tool 11 to travel along the guidewire 53; and wherein the retention body 31 may be configured to be movably attached relative to the housing 41 to allow the distal end 36 of the retention body 31 to advance toward the subject 1 to a deployed position.

In an embodiment, retention body 31 may be configured to be movably attached relative to the housing 41 to allow the distal end 36 of the retention body 31 to withdraw away from the subject 1 from the deployed position to a retracted position.

In an embodiment, the retention body 31 may be configured to be movably attached relative to the housing 41 to allow the distal end 36 of the retention body 31 to both advance toward the subject in a deployed positon and withdraw away from the subject 1 from the deployed position to a retracted position (and repeat between various iterations of such positions and any number of partial degrees of position thereof).

In an embodiment, any or all of the components discussed herein may be disposable or reusable, or any combination thereof.

The subcutaneous organ 5 of the subject 1 may include, but not limited thereto, a blood vessel, whereby the blood vessel may include an artery, vein, and capillary. The subcutaneous organ 5 of the subject 1 may include, but not limited thereto, a bone (which is considered a soft organ). In other applications, rather than a subcutaneous organ 5 of the subject 1, it may include, for example, a cavity space or the like of the subject 1.

In an embodiment, the cutting tool 11 may be at least one or more of any combination of the following: scalpel, bovie, knife, blade, other cutting instrument, or the like.

In an embodiment, the apparatus 21 may include at least one magnet 61 disposed on the housing 41, wherein the magnet 61 may have a distal end 66 and proximal end 68. In an embodiment, the magnet 61 is configured to magnetize the cutting tool 11 whereby the magnetization of the cutting tool 11 magnetically attracts the guidewire 53 (or other medical device) to the cutting tool 11 for tracking and aligning.

In an embodiment, the apparatus 21 may include at least one repository 49 disposed in the housing 41, wherein the repository is configured to contain at least one of the magnets 61 in the repository 49. In an embodiment, the magnet 61 may be attached to the outside of either or both sides of the housing 41. In an embodiment, a collection of magnets 61 may be attached to the outside of either or both sides of the housing 41 to create a magnetic gradient. In an embodiment, more than one repository 49 may be provided on one or both of the sides of the housing 41. In an embodiment, more than one magnet 61 may be disposed in a repository 49. The magnet 61 and repository 49 may be a variety of shapes, sizes and contours to meet the operational, magnetization, and anatomical demands and requirements. In an embodiment, a collection of magnets 61 may be disposed in a repository 49 or a collection of magnets 61 may be disposed within multiple repositories 49.

In an embodiment, the apparatus 21 may include a magnet 61 disposed on the retention body 31, wherein the magnet 61 may have a distal end 66 and proximal end 68. In an embodiment the magnet 61 may be configured to magnetize the cutting tool 11 whereby the magnetization of the cutting tool 11 magnetically attracts the guidewire 53 (or other medical device) to the cutting tool 11 for tracking and aligning. In an embodiment magnets may be disposed on both the housing and retention body.

In an embodiment, the magnet 61 or collection of magnets disposed on the housing 41 (and/or retention body 31) or in the repository 49 or repositories is configured to magnetically attract the guidewire 53 (or other medical device) to influence the guidewire 53, i.e., magnetically attract the guidewire for tracking and aligning. In an embodiment, the magnet 61 may be designed whereby its different portions (e.g., distal end 66, proximal end 68, or portion as designated, etc.) can provide the varying magnetic forces or magnetic gradient on the guidewire. In an embodiment, the magnet 61 may be designed whereby its distal end 66 provides the magnetic forces or magnetic gradient on the guidewire.

It should be appreciated, for example, that the magnet or magnets may shall include "non-rare earth magnets" and/or "rare earth magnets". For example, but not limited thereto, high iron content steel (i.e., less stainless and which are more likely to corrode) is less magnetic and therefore may be preferentially used with a bigger and/or stronger magnet. In an approach of embodiment, the degree of magnetism varies among a range of scalpels (or cutting tools) even though in the instances of single use environment, corrosion is not as much of a concern.

In an embodiment, the guidewire holder member 51 is at least one or more of any combination of the following: aperture, hook, loop, conduit, groove, notch, slit, lumen, bore, orifice, aperture, or channel. In an embodiment, the guidewire holder member 51 may be uncovered (e.g., "unroofed") to provide open access so as to allow for a magnetized scalpel and the guidewire to track one another without an overlying interface. In an embodiment, the guidewire holder member 51 may be uncovered (e.g., "unroofed") to provide open access so as to allow for a magnetized scalpel and the guidewire to track one another without an overlying interface (or cover) so as to make direct contact with one another (i.e., the scalpel or cutting tool making direct contact with the guidewire).

Figure 6A:
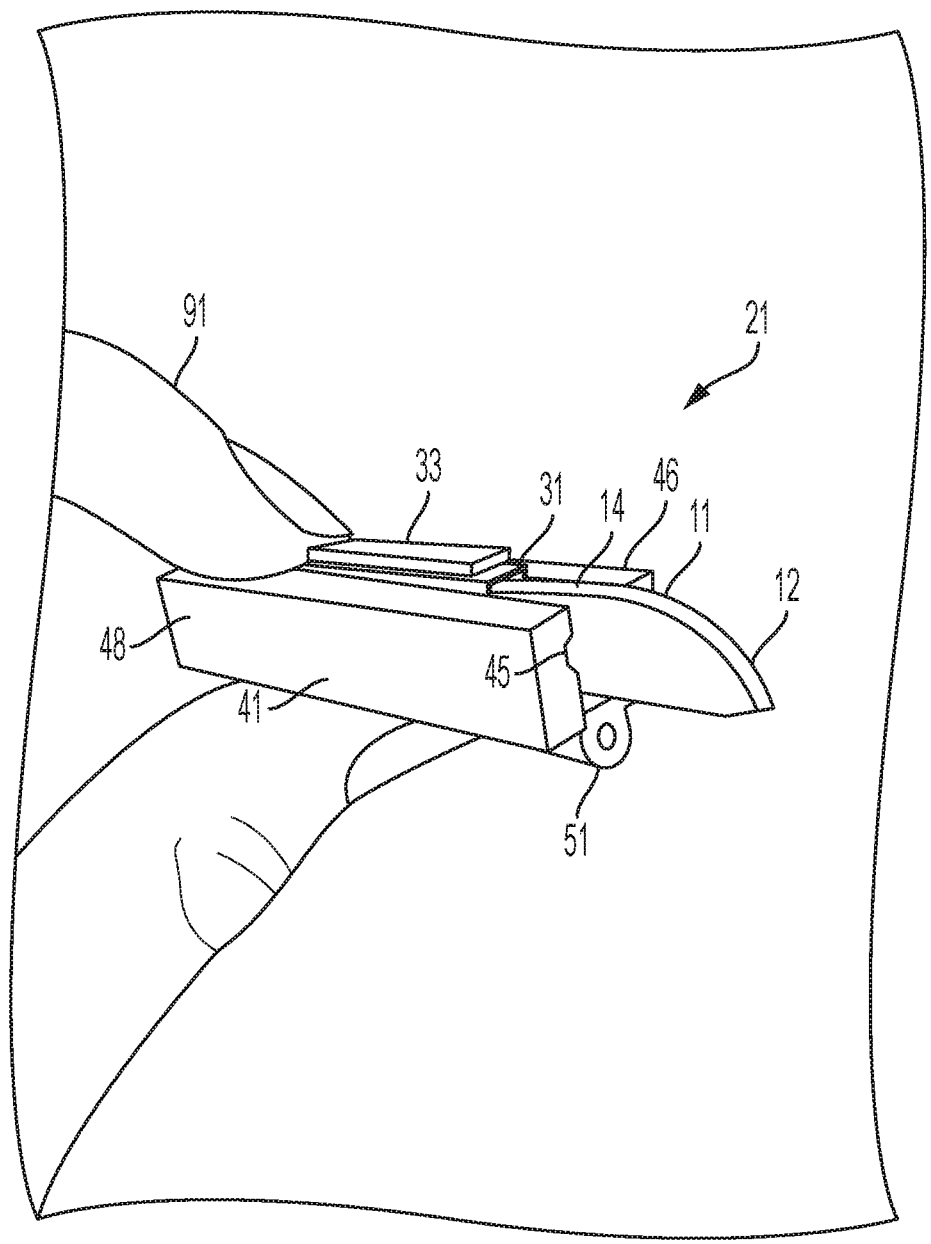
FIG. 6A schematically illustrates a perspective side-distal view of an embodiment of the surgical incision apparatus with the retention body and cutting tool in a deployed position while held by a user whereby the guidewire holder member is covered.
Figure 6B:
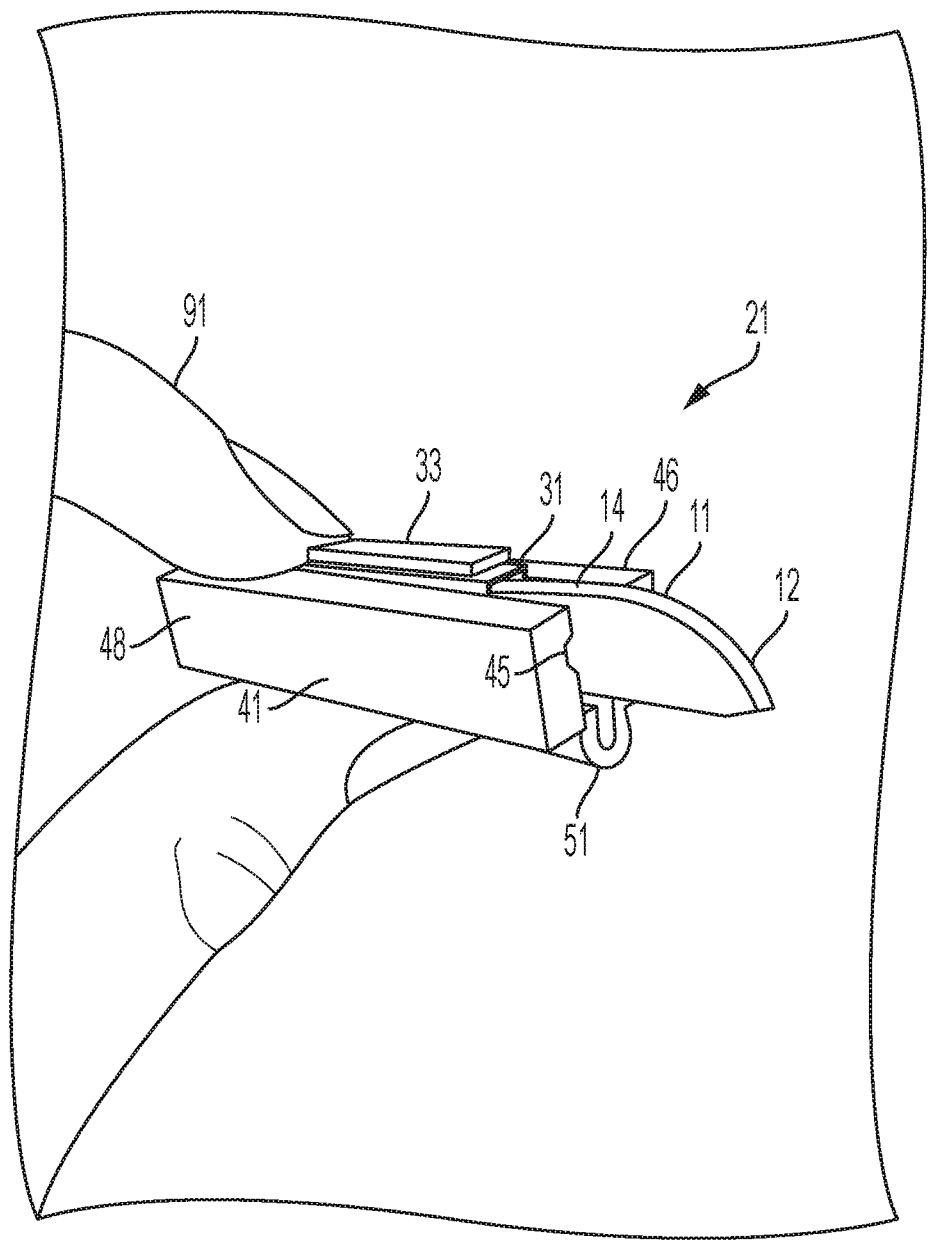
FIG. 6B schematically illustrates a perspective side-distal view of an embodiment of the surgical incision apparatus with the retention body and cutting tool in a deployed position while held by a user whereby the guidewire holder member is uncovered.
Figure 7:
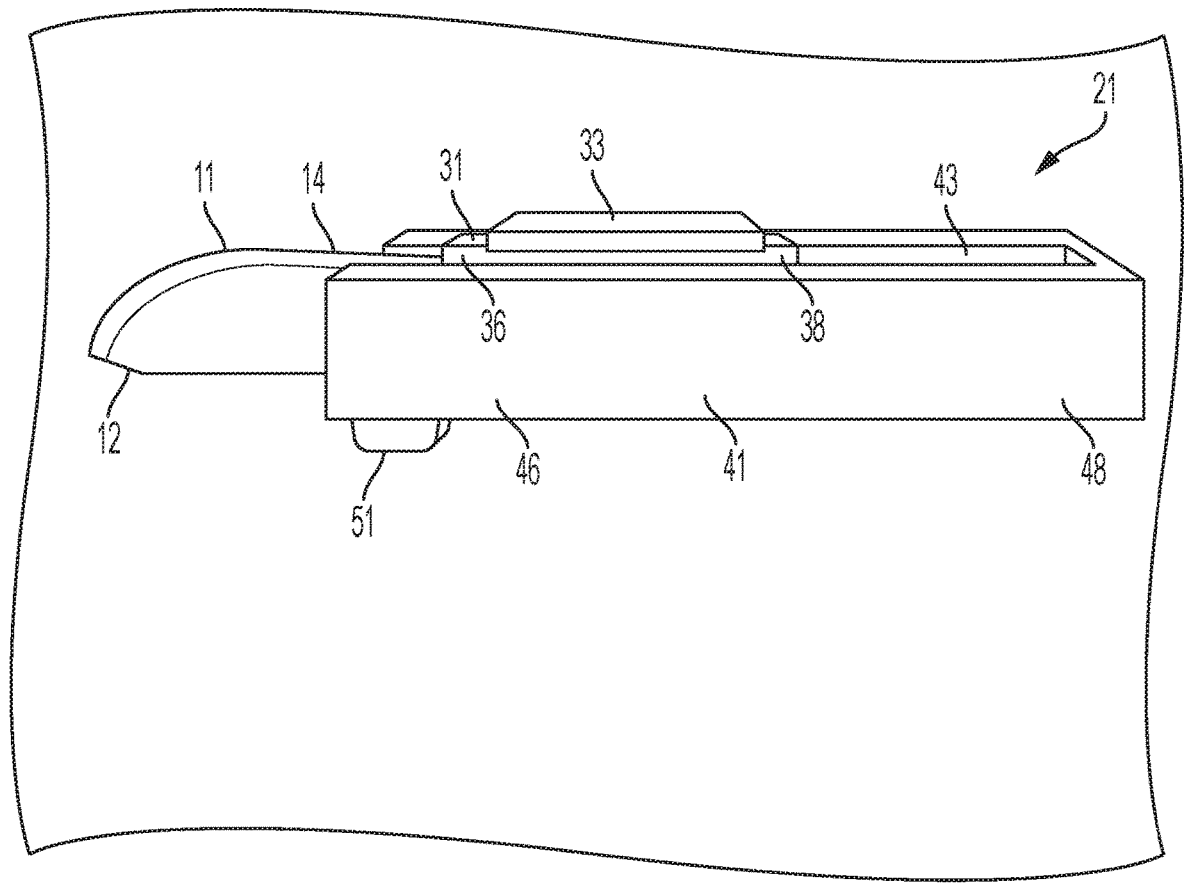
FIG. 7 schematically illustrates a perspective side view of an embodiment of the surgical incision apparatus with the retention body and cutting tool in a deployed position.
Figure 8:
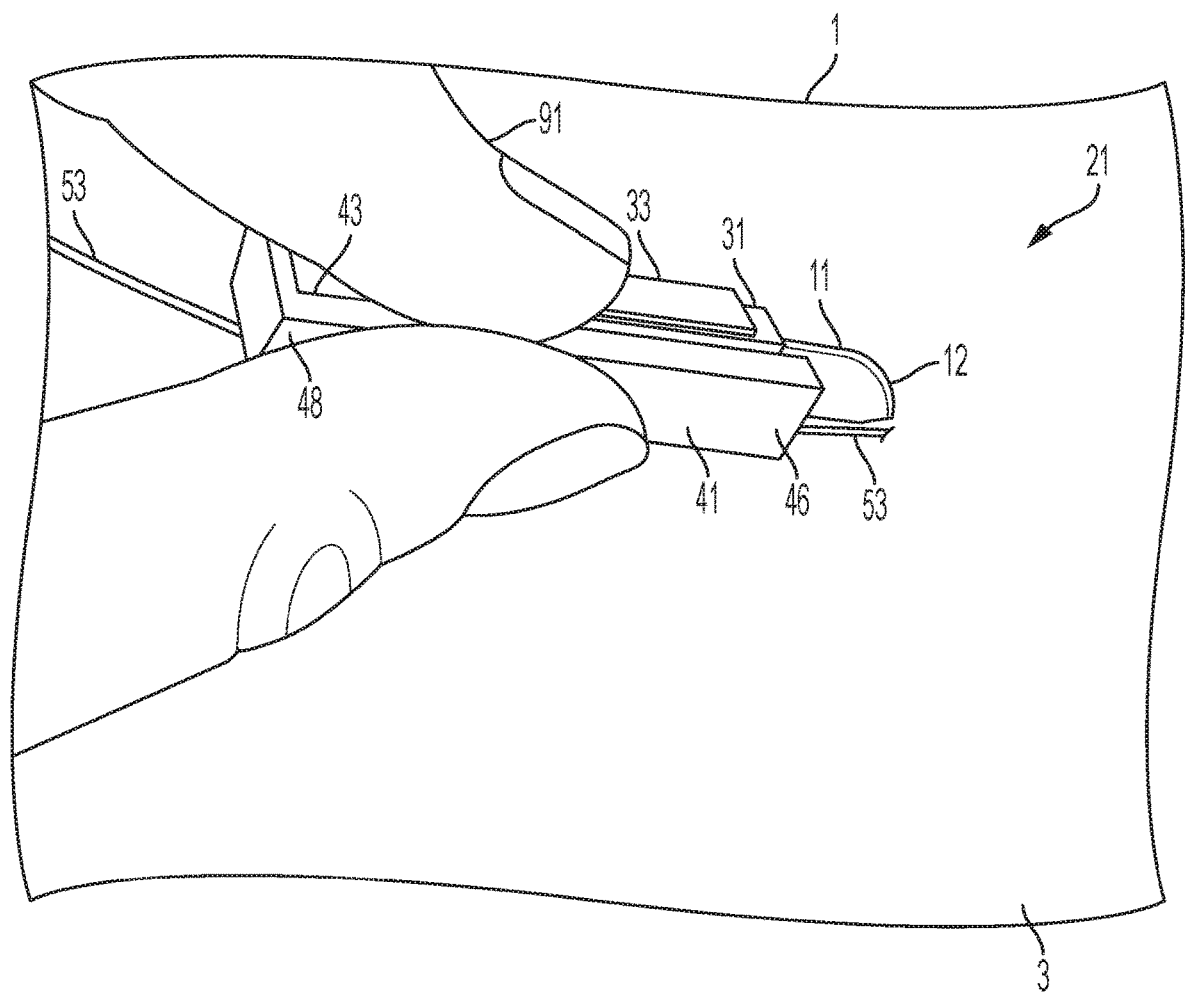
FIG. 8 schematically illustrates a perspective side-proximal view of an embodiment of the surgical incision apparatus with the retention body and cutting tool in a deployed position held by a user while in use with a guidewire at the imminent incision site of the subject.
Figure 9:
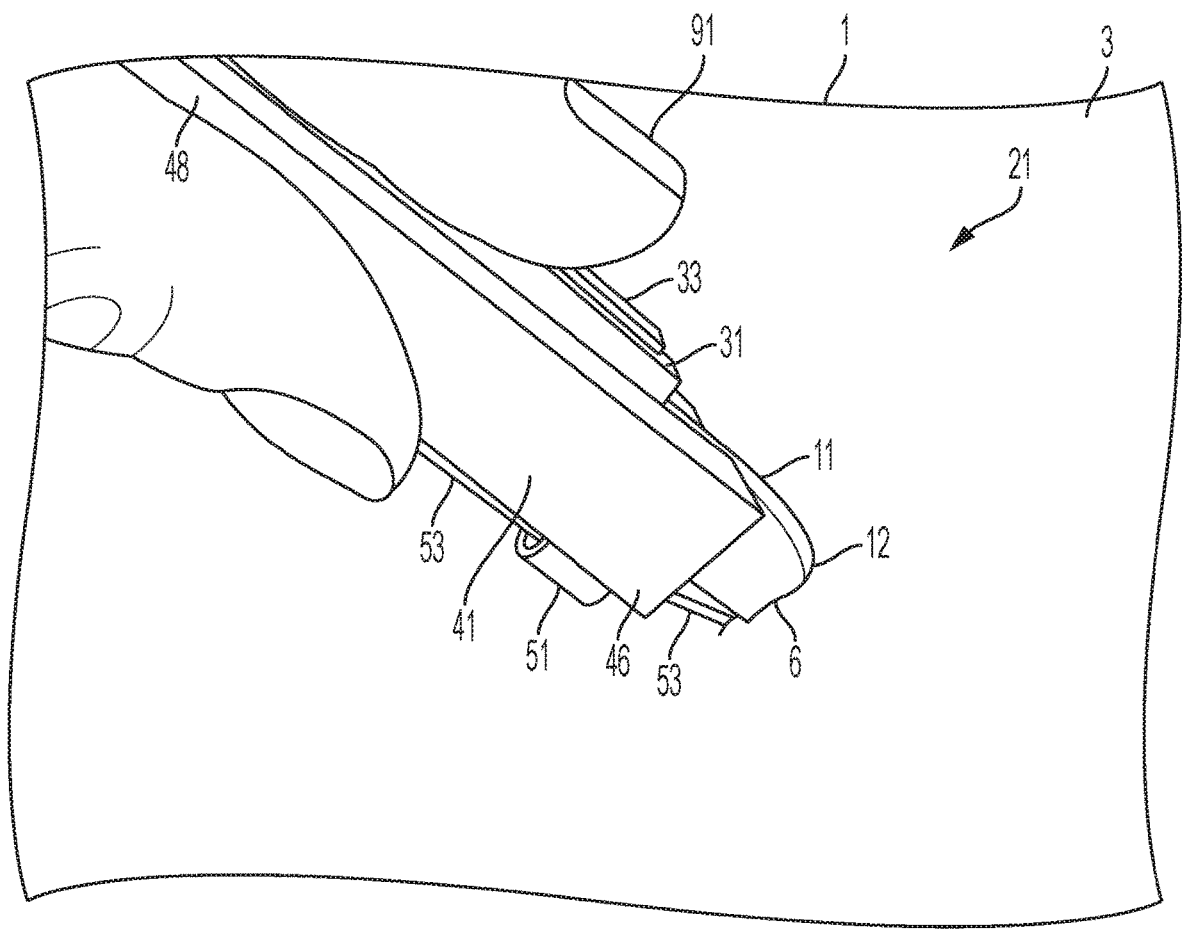
FIG. 9 schematically illustrates a perspective side-proximal view of an embodiment of the surgical incision apparatus with the retention body and cutting tool in a deployed position held by a user while in use with a guidewire during an incision being implemented on the subject.

In an embodiment, for example, the guidewire holder member 51 may partially cover over the guidewire 53 or completely cover over the guidewire 53 that would be installed therein. In an embodiment, for example, but not limited thereto, FIG. 6A schematically illustrates the guidewire holder member 51 that is covered between the cutting tool 11 and the guidewire (not shown). In an embodiment, for example, but not limited thereto, FIG. 6B schematically illustrates the guidewire holder member 51 that is uncovered or exposed between the cutting tool 11 and guidewire (not shown) thus enabling the cutting tool 11 to have access to the guidewire (not shown) therein.

In an embodiment, the housing 41 may include a housing channel 43 to receive the retention body 31 disposed therein to provide for the retention body 31 being movably attached relative to the housing 41 to allow the distal end 36 of the retention body 31 to advance toward the subject 1 to a deployed position.

In an embodiment, the housing 41 may include a housing channel 43 to receive the retention body 31 disposed therein to provide for the retention body 31 being movably attached relative to the housing 41 to allow the distal end 36 of the retention body 31 to withdraw away from the subject 1 to a retracted position.

In an embodiment, the housing 41 may include a housing channel 43 to receive the retention body 31 disposed therein to provide for the retention body 31 being movably attached relative to the housing 41 to allow the distal end 36 of the retention body 31 to both advance toward the subject to a deployed position and withdraw away from the subject 1 to a retracted position (and repeat between various iterations of such positions and any number of partial degrees of position thereof).

In an embodiment, the housing channel 43 may include a housing track 45 disposed thereon; and the retention body 31 may include a retention body track 35 disposed thereon. In an embodiment, housing track 45 and retention body track 35 are connectably joinable with one another wherein the retention body 31 advancement is along the joined housing track 45 and the retention body track 35.

Figure 10:
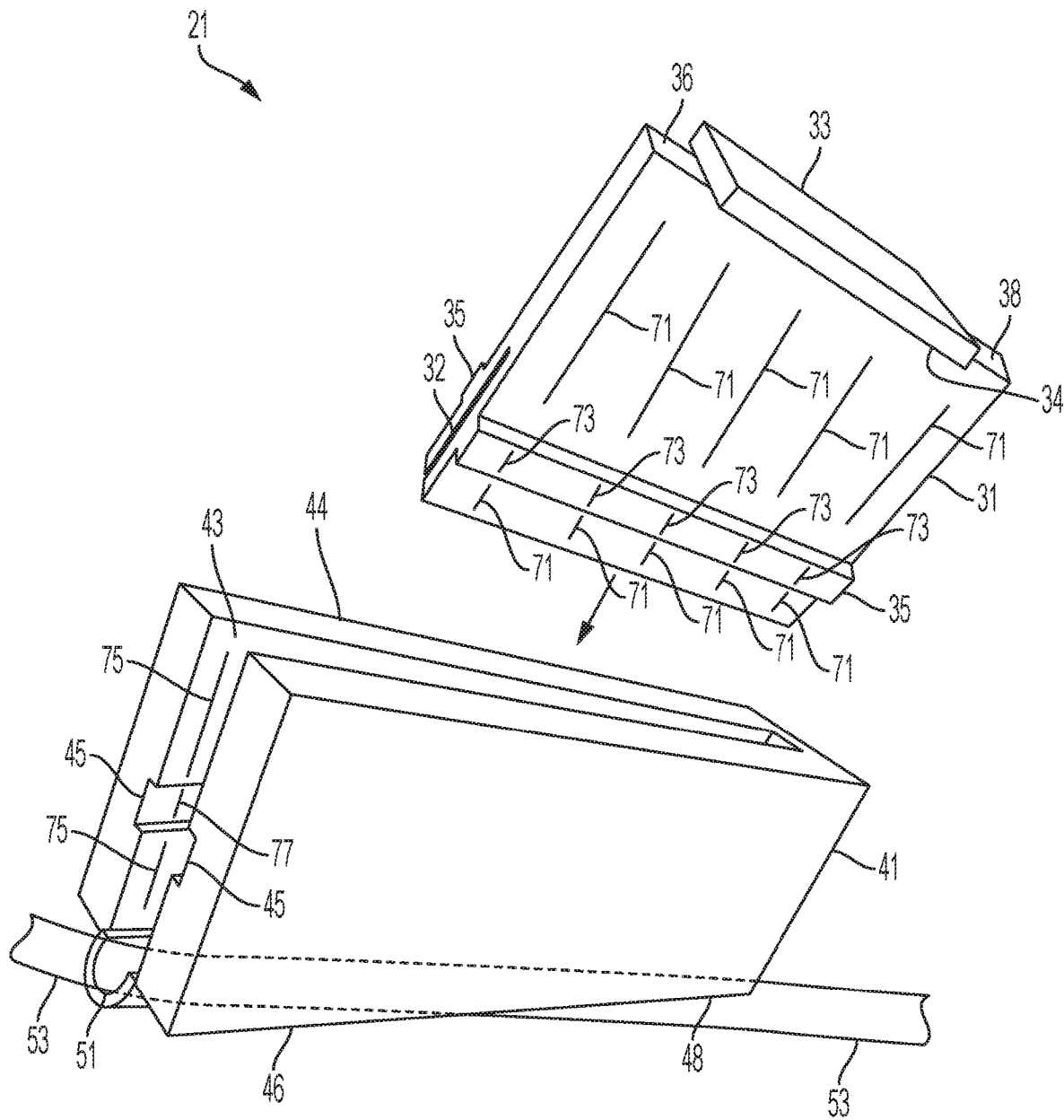
FIG. 10 schematically illustrates an exploded view of an embodiment of the surgical incision apparatus with the retention body available to be inserted into the housing while in use with a guidewire, and wherein check structures are provided on the tracks, housing channel, and retention body.
Figure 11:
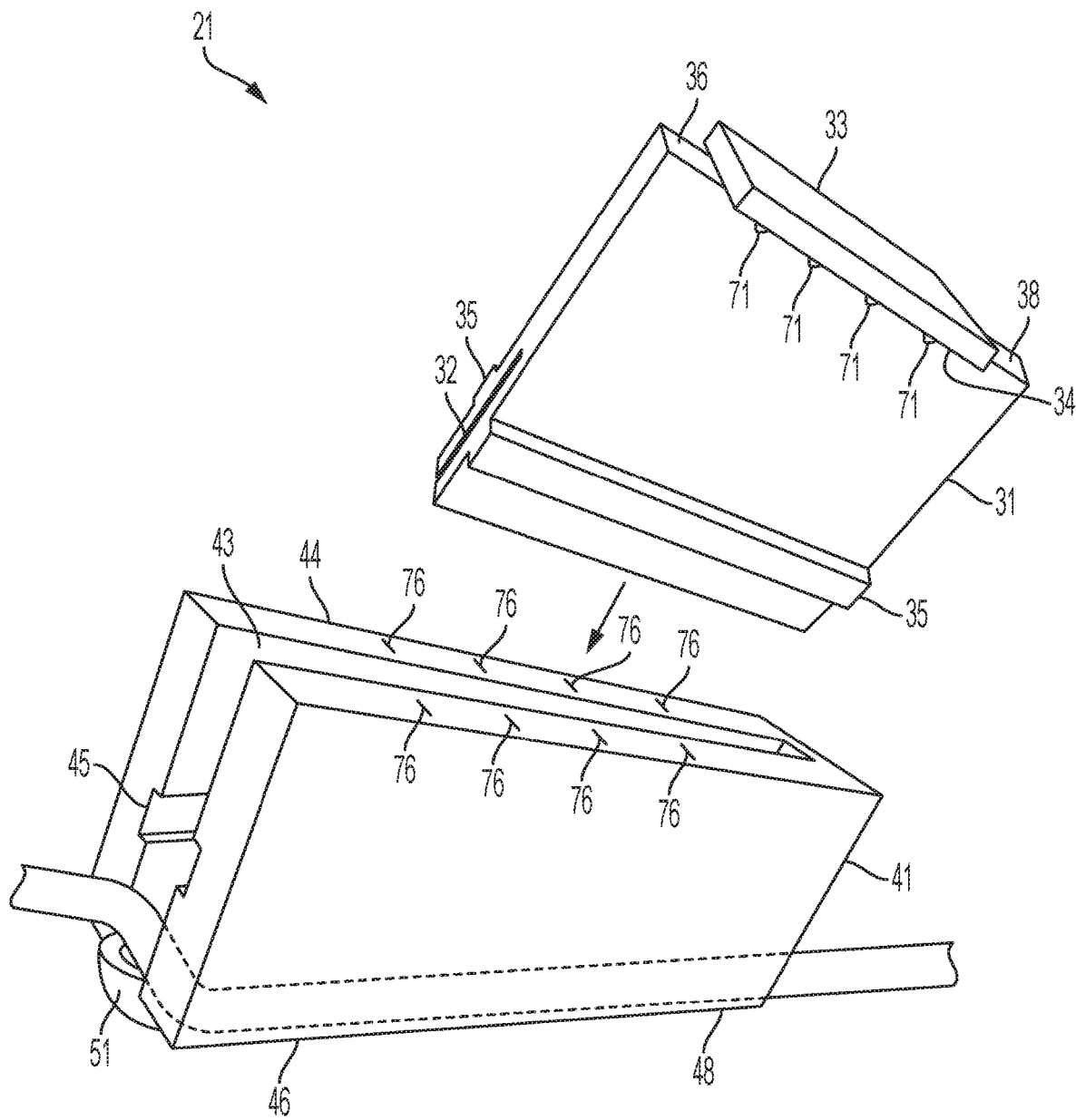
FIG. 11 schematically illustrates an exploded view of an embodiment of the surgical incision apparatus with the retention body available to be inserted into the housing while in use with a guidewire, and wherein check structures are provided on the upper side of the housing and the under portion of the upper side of the retention body.

In an embodiment, at least one check structure is disposed on the housing track 45 defining a housing track check structure 77 and at least one check structure is disposed on the retention body track 35 defining a retention body track check structure 73 (as shown, for example, in FIG. 10). It should be appreciated that retention body track structures 73 may also be implemented on the opposite side of the retention body 31, but not shown due to the limitations of the illustration. Due to the limitation of the illustration of FIG. 10 only a set of housing track check structures 77 are shown on one side of the housing channel 43, but it should be appreciated that a plurality may be implemented along the housing channel 43 (on both sides of the housing channel 43) across the distal-proximal span. The housing track check structure 77 and the retention body track check structure 73 are configured to contact one another during the advancement of the distal end 36 of the retention body 31 toward the subject 1 to a deployed position, wherein the contact provides feedback to the user 91 of the corresponding location of the retention body 31 (and corresponding cutting tool). The housing track check structure 77 and the retention body track check structure 73 are configured to contact one another during the advancement of the distal end 36 of the retention body 31 toward the subject 1 and away from the subject 1 to a retracted position (and which can repeat between various iterations of such positions and any number of partial degrees of position thereof), wherein the contact provides feedback to the user 91 of the corresponding location of the retention body 31 (and corresponding cutting tool 11).

In an embodiment, the housing track check structure 77 and/or retention body track check structure 73 may comprise one or more of any combination of the following: ridge, bump, lip, ledge, tab, notch, protrusion, groove, indentation, or the like.

In an embodiment, the retention body 31 includes a wall and wherein at least one check structure is disposed on the wall of the retention body 31 defining a retention body check structure 71 and the housing channel 43 comprises a wall and wherein at least one check structure is disposed on the wall of the housing channel 43 defining a housing channel check structure 75 (as shown, for example, in FIG. 10). Due to the limitation of the illustration of FIG. 10, only a set of housing channel check structures 75 are shown on one side of the housing channel 43, but it should be appreciated that a plurality may be implemented along the housing channel 43 (on both sides of the housing channel 43) across the distal-proximal span. The retention body check structure 71 and the housing channel check structure 75 are configured to contact one another during the advancement of the distal end 36 of the retention body 31 toward the subject 1 to a deployed position, wherein the contact provides feedback to the user 91 of the corresponding location of the retention body 31 (and corresponding cutting tool 11). The retention body check structure 71 and the housing channel check structure 75 are configured to contact one another during the advancement of the distal end 36 of the retention body 31 toward the subject 1 to a deployed position and away from the subject 1 to a retracted position (and repeat between various iterations of such positions and any number of partial degrees of position thereof), wherein the contact provides feedback to the user 91 of the corresponding location of the retention body 31 (and corresponding cutting tool 11).

In an embodiment, the housing channel check structure 75 and/or retention body check structure 71 may comprise one or more of any combination of the following: ridge, bump, lip, ledge, tab, notch, protrusion, groove, indentation, or the like.

In an embodiment, the apparatus may be implemented with the retention body track check structure 73, housing track check structure 77, retention body check structure 71, and housing channel check structure 75.

In an embodiment, any of the check structures may be used to lock or fix the retention body 31 and/or cutting tool 11 in place at any of the intervals allowing for precise incision depth, control, safety and accuracy.

Figure 17:
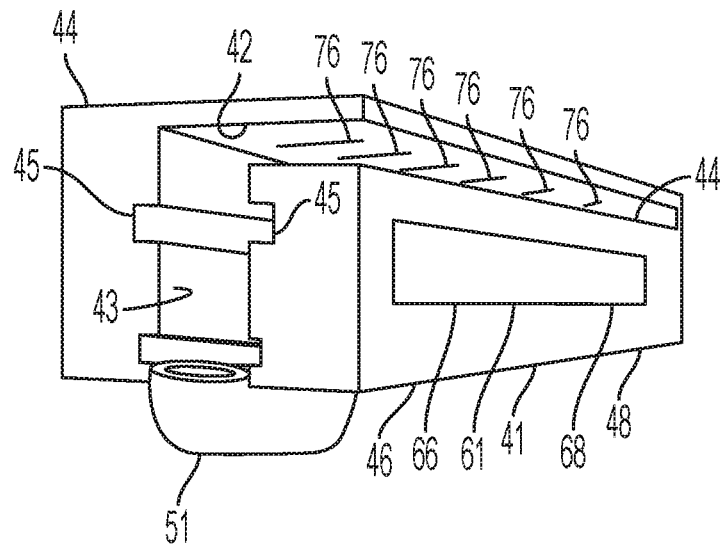
FIG. 17 schematically illustrates a perspective side-distal view of an embodiment of the surgical incision apparatus that includes the housing without the retention body, and further includes a magnet disposed oppositely on either side of the housing (wherein only one side is visible in current illustration), as well as check structures disposed on the under portion of the upper side of the housing.
Figure 18:
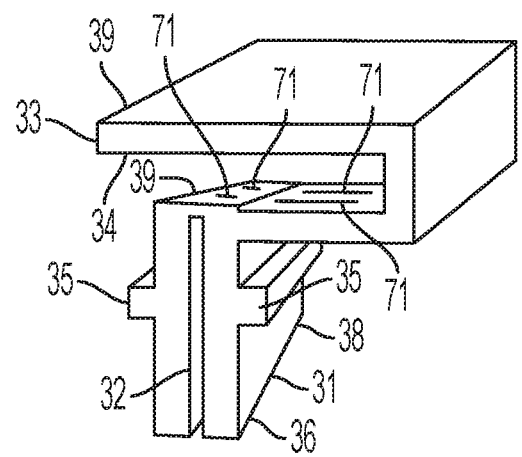
FIG. 18 schematically illustrates a perspective side-distal view of an embodiment of the surgical incision apparatus that includes the retention body without the housing, and further includes check structures disposed on an upper side of the retention body.

In an embodiment, the retention body 31 may include an upper side 39 and wherein at least one check structure is disposed on the upper side 39 of the retention body 31 defining a retention body upper side check structure 71 and the housing 41 may include an under portion 42 of an upper side 44 and wherein at least one check structure is disposed on the under portion 42 of the upper side 44 of the housing 41 defining a housing under portion-upper side check structure 76 (as shown, for example, in FIGS. 17 and 18). The retention body upper side check structure 71 and the housing under portion-upper side check structure 76 are configured to contact one another during the advancement of the distal end 36 of the retention body 31 toward the subject 1 to a deployed position and away from the subject 1 to a retracted position (and repeat between various iterations of such positions and any number of partial degrees of position thereof), wherein the contact provides feedback to the user 91 of the corresponding location of the retention body 31 (and corresponding cutting tool 11).

In an embodiment, the retention body upper side check structure 71 or housing under portion-upper side check structure 76 comprises one or more of any combination of the following: ridge, bump, lip, ledge, tab, notch, protrusion, groove, indentation, or the like.

Figure 15:
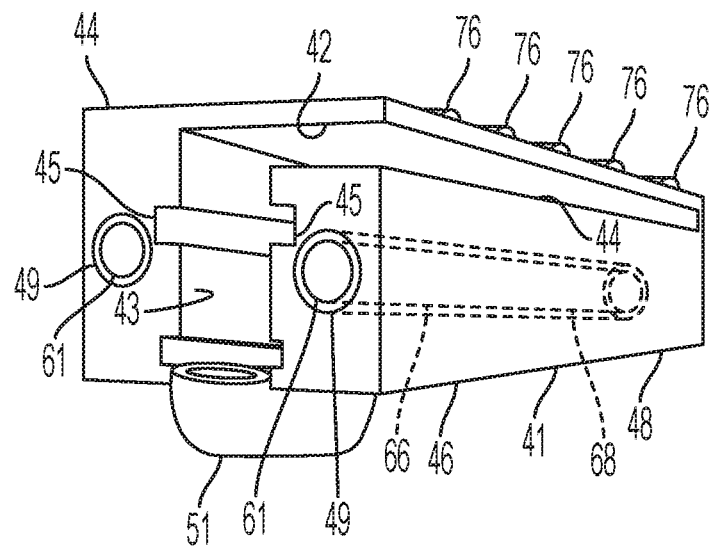
FIG. 15 schematically illustrates a perspective side-distal view of an embodiment of the surgical incision apparatus that includes the housing without the retention body, and further includes a magnet disposed in a magnet repository in opposite sides of the housing, as well as check structures disposed on upper side of the housing.
Figure 16:
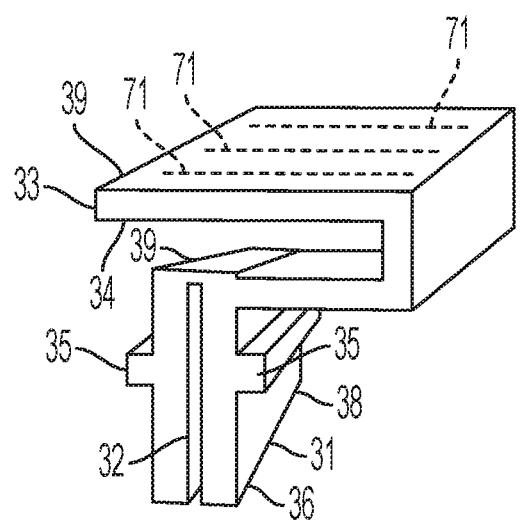
FIG. 16 schematically illustrates a perspective side-distal view of an embodiment of the surgical incision apparatus that includes the retention body without the housing, and further includes check structures disposed on an under portion of the upper side of the retention body.

In an embodiment, the retention body 31 may include an under portion 34 of an upper side 39 and wherein at least one check structure is disposed on the under portion 34 of the upper side 39 of the retention body 31 defining a retention body under portion-upper side check structure 71 and the housing 41 may include an upper side 44 and wherein at least one check structure is disposed on the upper side 44 of the housing 41 defining a housing upper side check structure 76 (as shown, for example, in FIGS. 15 and 16). As intended by the illustration, the retention body under portion-upper side check structures 71 are represented as dashed lines as they would not be visible with the current view (due to being located on the underside). The retention body under portion-upper side check structure 71 and the housing upper side check structure 76 are configured to contact one another during the advancement of the distal end of the retention body toward the subject to a deployed position and away from the subject 1 to a retracted position (and repeat between various iterations of such positions and any number of partial degrees of position thereof), wherein the contact provides feedback to the user 91 of the corresponding location of the retention body 31 (and corresponding cutting tool 11).

In an embodiment, the retention body upper side check structure 71 or housing upper side check structure 76 may include one or more of any combination of the following: ridge, bump, lip, ledge, tab, notch, protrusion, groove, indentation, or the like.

Figure 2:
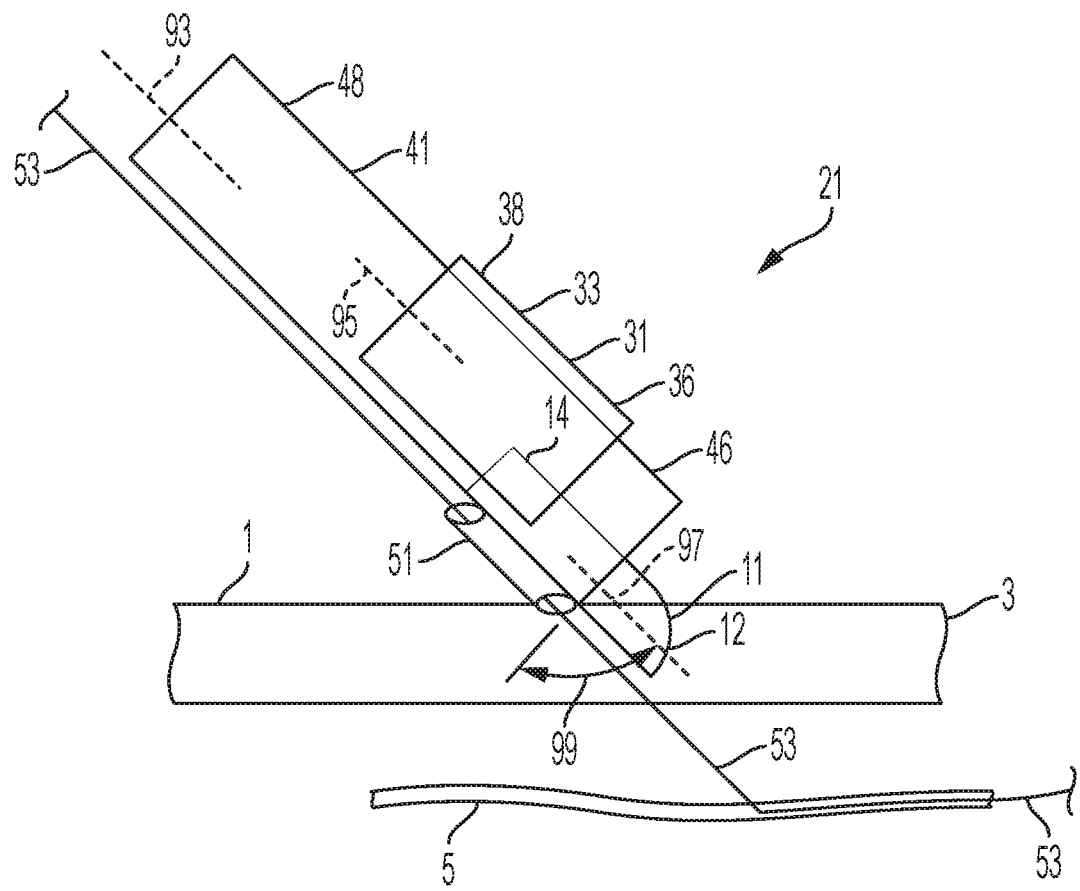
FIG. 2 schematically illustrates an embodiment of the surgical incision apparatus with the retention body and cutting tool in a deployed position in an environment of the subject.
Figure 3:
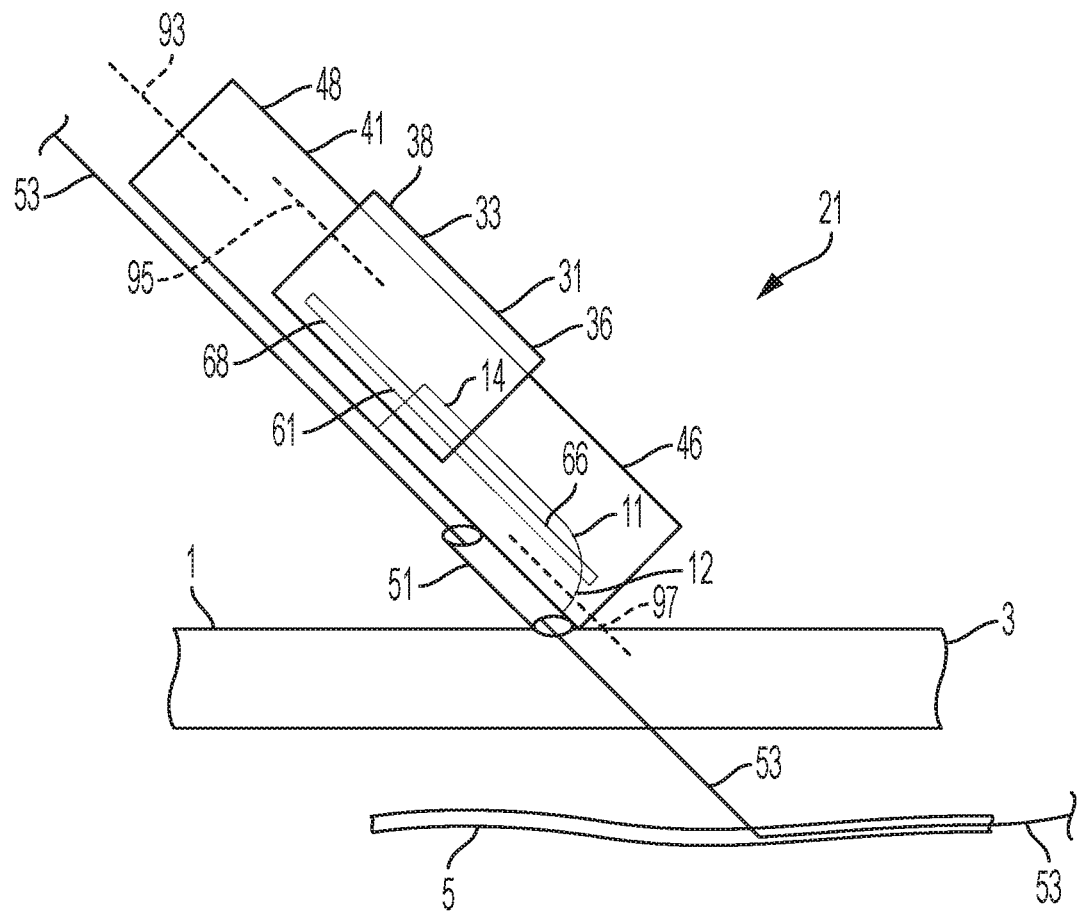
FIG. 3 schematically illustrates an embodiment of the surgical incision apparatus, provided with a magnet, with the retention body and cutting tool in a retracted position in an environment of the subject.
Figure 4:
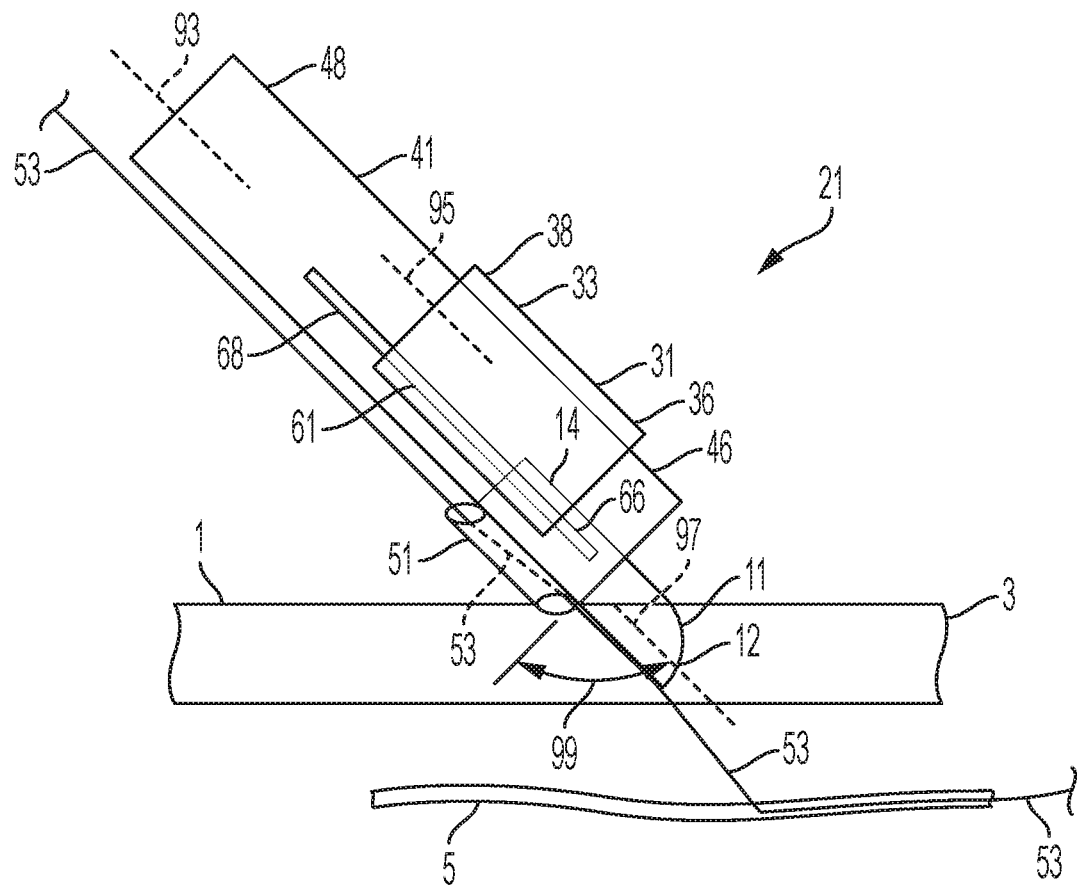
FIG. 4 schematically illustrates an embodiment of the surgical incision apparatus, provided with a magnet, with the retention body and cutting tool in a deployed position in an environment of the subject, and wherein the guidewire is magnetically attracted to the magnetized cutting tool.
Figure 5:
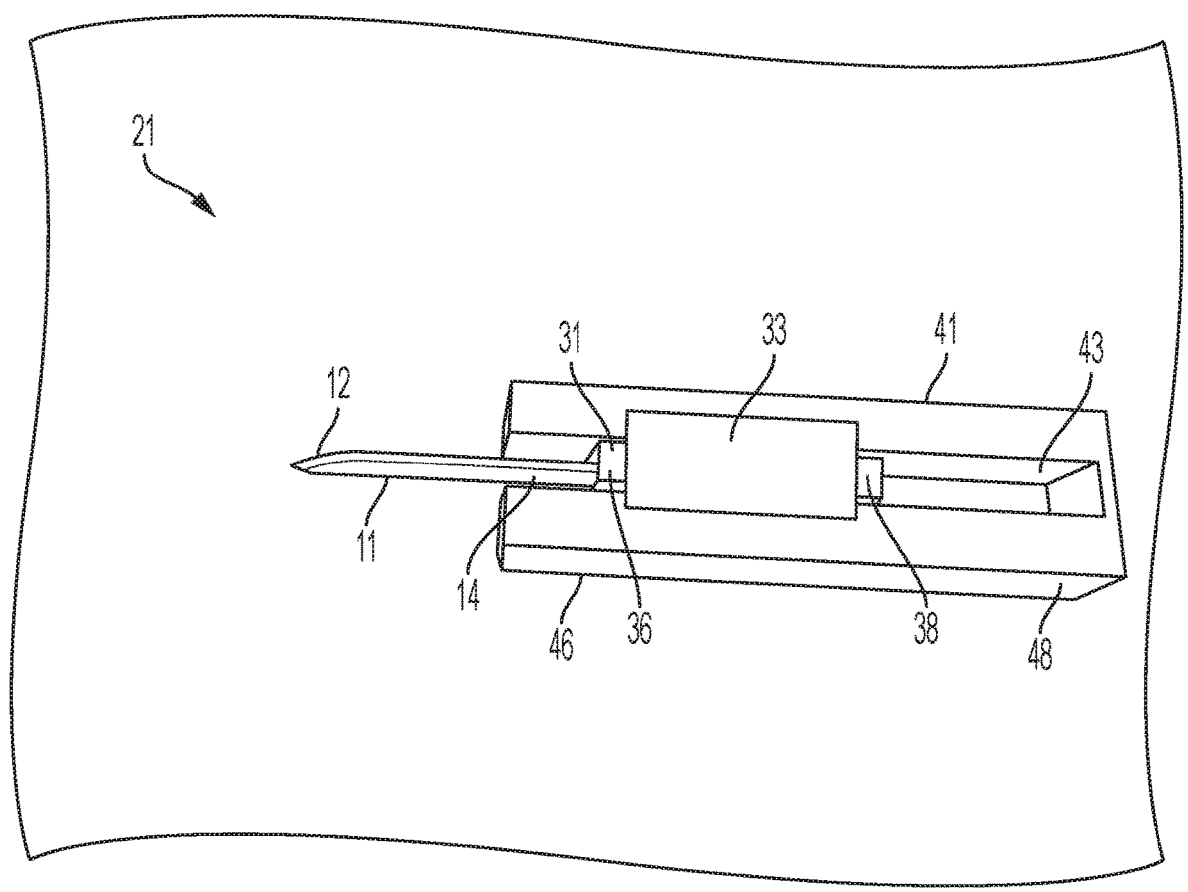
FIG. 5 schematically illustrates a perspective top view of an embodiment of the surgical incision apparatus with the retention body and cutting tool in a deployed position.

In an embodiment, the retention body 31 is configured wherein said advancement of said distal end 36 of said retention body 31 is in substantially in the direction going from the proximal end 38 of the retention body to the distal end 36 of the retention body 31 whereby the advancement direction provides for approximately a ninety degree angle 99 with the distal end 46 of the housing 41 (as shown, for example, in FIGS. 2 and 4). Still referring to FIGS. 2 and 4, the housing 41 is portrayed with a longitudinal axis 93, the retention body 31 is portrayed with a longitudinal axis 95, and the cutting tool 11 is portrayed with a longitudinal axis 97. Still referring to FIGS. 2 and 4, for example, rather than the angle 99 being ninety degrees, it may be less than or greater than ninety degrees. For example, the angle 99 may be in the range of about 80 degrees to about 100 degrees or any number or fraction subsumed within this range. Moreover, alignment may be implemented in the opposite direction such as having the angle 99 being in the range of about 90 degrees to about 150 degrees or any number or fraction subsumed within this range.

Figure 13:
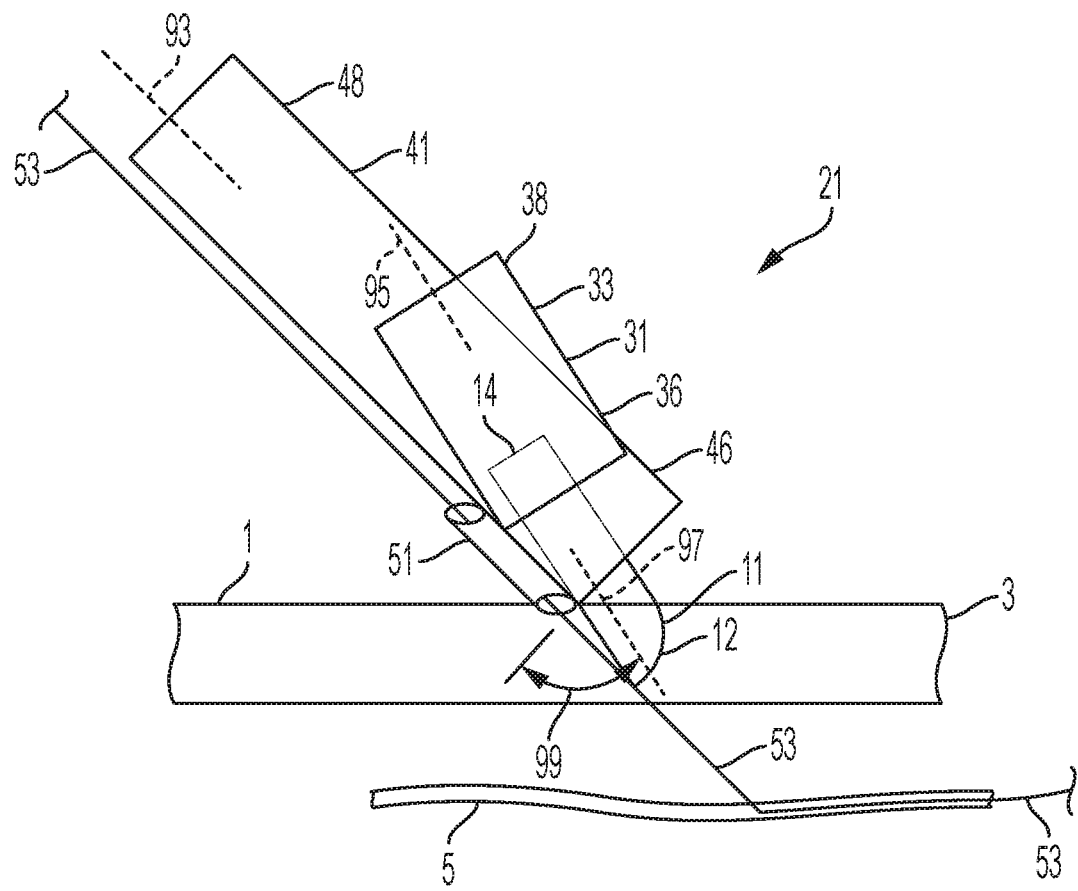
FIG. 13 schematically illustrates an embodiment of the surgical incision apparatus with the retention body and cutting tool in a deployed position in an environment of the subject, and wherein the retention body and cutting tool are aligned in an acute angle.
Figure 14:
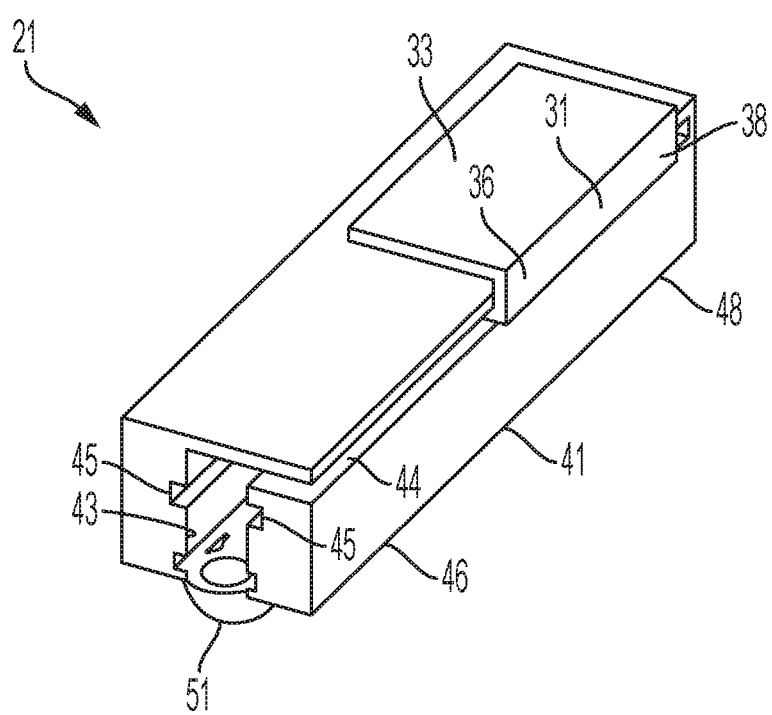
FIG. 14 schematically illustrates a perspective side-distal view of an embodiment of the surgical incision apparatus that includes the housing with the retention body in a retracted position without possession of a cutting tool.

In an embodiment, the retention body is configured wherein said advancement of said distal end 36 of said retention body 31 is in substantially in the direction going from the proximal end 38 of the retention body 31 to the distal end 36 of the retention body 31 whereby the advancement direction provides for an acute angle 99 of the cutting tool 11 with the distal end 46 of the housing 48 (as shown, for example, in FIG. 13). Still referring to FIG. 13, the housing 41 is portrayed with a longitudinal axis 93, the retention body 31 is portrayed with a longitudinal axis 95, and the cutting tool 11 is portrayed with a longitudinal axis 97. As illustrated, the longitudinal axis 95 of the retention body 31 and the longitudinal axis 97 of the cutting tool 11 are aligned in substantially the same axis. Still referring to FIG. 13, for example, the angle 99 of the cutting tool 11 may be a variety of angles. For example, the angle 99 may be in the range of about 90 degrees to about 30 degrees or any number or fraction subsumed within this range. For example, the angle 99 may be in the range of about 90 degrees to about 10 degrees or any number or fraction subsumed within this range.

In an embodiment, the retention body is configured wherein said securement of said cutting tool 11 to the retention body provides a specified alignment of said cutting tool 11 relative to said retention body 31 whereby said advancement of said distal end 36 of said retention body 31 is in substantially in the direction going from the proximal end 38 of the retention body 31 to the distal end 36 of the retention body 31 whereby the alignment of said cutting tool 11 provides for approximately about a ninety degree angle 99 with the distal end of the housing (as shown, for example, in FIGS. 2 and 4). Still referring to FIGS. 2 and 4, the housing 41 is portrayed with a longitudinal axis 93, the retention body 31 is portrayed with a longitudinal axis 95, and the cutting tool 11 is portrayed with a longitudinal axis 97. Still referring to FIGS. 2 and 4, for example, rather than the angle 99 being ninety degrees, it may be less than or greater than ninety degrees. For example, the angle 99 may be in the range of about 80 degrees to about 100 degrees or any number or fraction subsumed within this range. Moreover, alignment may be implemented in the opposite direction such as having the angle 99 being in the range of about 90 degrees to about 150 degrees or any number or fraction subsumed within this range.

Figure 12:
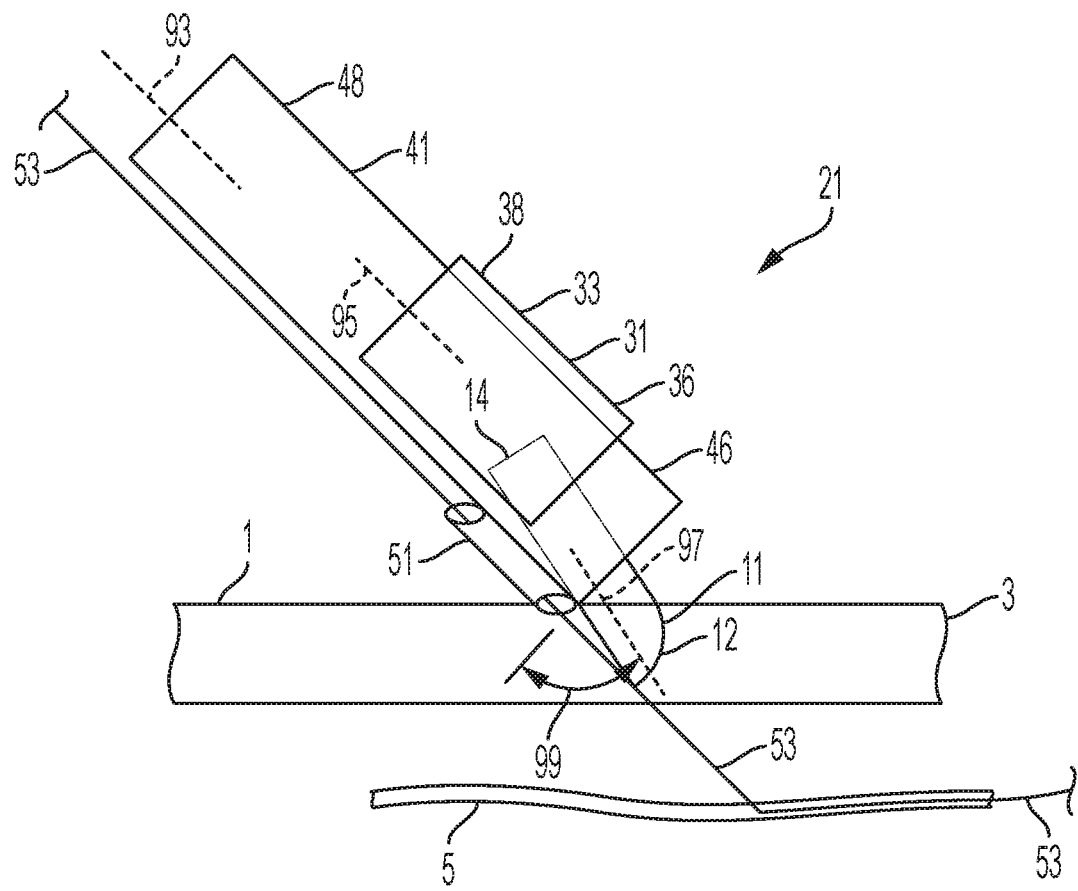
FIG. 12 schematically illustrates an embodiment of the surgical incision apparatus with the retention body and cutting tool in a deployed position in an environment of the subject, and wherein the cutting tool is aligned in an acute angle.

In an embodiment, the retention body 31 is configured wherein said securement of said cutting tool 11 to the retention body 31 provides a specified alignment of said cutting tool 11 relative to said retention body 31 whereby said advancement of said distal end 36 of said retention body 31 is in substantially in the direction going from the proximal end 38 of the retention body 31 to the distal end 36 of the retention body 31 whereby the alignment of said cutting tool 11 provides for an acute angle 99 with the distal end 46 of the housing 41 (as shown, for example, in FIGS. 12 and 13). Still referring to FIGS. 12 and 13, the housing 41 is portrayed with a longitudinal axis 93, the retention body 31 is portrayed with a longitudinal axis 95, and the cutting tool 11 is portrayed with a longitudinal axis 97. As illustrated in FIG. 12, the longitudinal axis 95 of the retention body 31 and the longitudinal axis 97 of the cutting tool 11 are offset relative to each other (i.e., not on the same axis). Still referring to FIGS. 12 and 13, for example, the angle 99 may be a variety of angles. For example, the angle 99 may be in the range of about 90 degrees to about 30 degrees or any number or fraction subsumed within this range. For example, the angle 99 may be in the range of about 90 degrees to about 10 degrees or any number or fraction subsumed within this range.

An aspect of an embodiment of the present invention apparatus provides, among other things, the ability, while using a single hand by the user, to simultaneously either deploy or retract the cutting tool while traversing the guide wire, and position the housing by utilizing the mobility of the retention body.

An aspect of an embodiment of the present invention apparatus provides, among other things, the ability, while using a single hand by the user, to simultaneously either deploy or retract the cutting tool while magnetically attracting the guidewire or other medical device to the cutting tool while traversing the guide wire, and positioning the housing by utilizing the mobility of the retention body.

An aspect of an embodiment of the present invention apparatus provides for a variety of angles of which the cutting tool 11, retention body 31, and/or housing 41 may be specified for advancement and withdrawal prior to use and/or during use.

EXAMPLES

Practice of an aspect of an embodiment (or embodiments) of the invention will be still more fully understood from the following examples and experimental results, which are presented herein for illustration only and should not be construed as limiting the invention in any way.

Example 1. A surgical incision apparatus for puncturing a cutaneous layer of a subject for providing guided access to a subcutaneous organ or subcutaneous cavity of the subject, the apparatus comprising:
- a retention body configured for securing a cutting tool therein, wherein the retention body having a distal end and proximal end;
- a housing configured for receiving the retention body, wherein the housing having a distal end and proximal end;
- a guidewire holder member disposed on the housing configured for receiving a guidewire therein and aligning with the guidewire to allow the cutting tool to travel along the guidewire; and
- wherein the retention body is configured to be movably attached relative to the housing to allow the distal end of the retention body to advance toward the subject to a deployed position.

Example 2. The apparatus of example 1, wherein the retention body is configured to be movably attached relative to the housing to allow the distal end of the retention body to withdraw away from the subject from the deployed position to a retracted position.

Example 3. The apparatus of example 1 (as well as subject matter in whole or in part of example 2), further comprising the cutting tool provided together in a kit with the apparatus.

Example 4. The apparatus of example 1 (as well as subject matter of one or more of any combination of examples 2-3, in whole or in part), wherein the cutting tool is at least one or more of any combination of the following: scalpel, bovie, knife, blade, or other cutting instrument.

Example 5. The apparatus of example 1 (as well as subject matter of one or more of any combination of examples 2-4, in whole or in part), further comprising the guidewire provided together in a kit with the apparatus.

Example 6. The apparatus of example 1 (as well as subject matter of one or more of any combination of examples 2-5, in whole or in part), further comprising at least one magnet disposed on the housing, wherein the magnet having a distal end and proximal end, and wherein the magnet is configured to magnetize the cutting tool whereby the magnetization of the cutting tool magnetically attracts the guidewire.

Example 7. The apparatus of example 6 (as well as subject matter of one or more of any combination of examples 2-5, in whole or in part), further comprising at least one repository disposed in the housing, wherein the repository is configured contain at least one the magnet in the repository.

Example 8. The apparatus of example 6 (as well as subject matter of one or more of any combination of examples 2-5 or 7, in whole or in part), wherein the at least one magnet is configured to magnetically attract the guidewire.

Example 9. The apparatus of example 1 (as well as subject matter of one or more of any combination of examples 2-8, in whole or in part), further comprising at least one magnet disposed on the housing, wherein the magnet having a distal end and proximal end, and wherein the magnet is configured to magnetically attract the guidewire.

Example 10. The apparatus of example 1 (as well as subject matter of one or more of any combination of examples 2-9, in whole or in part), further comprising at least one magnet disposed on the retention body, wherein the magnet having a distal end and proximal end, and wherein the magnet is configured to magnetize the cutting tool whereby the magnetization of the cutting tool magnetically attracts the guidewire.

Example 11. The apparatus of example 10 (as well as subject matter of one or more of any combination of examples 2-9, in whole or in part), wherein the at least one magnet is configured to magnetically attract the guidewire.

Example 12. The apparatus of example 1 (as well as subject matter of one or more of any combination of examples 2-11, in whole or in part), further comprising at least one magnet disposed on the retention body, wherein the magnet having a distal end and proximal end, and wherein the magnet is configured to magnetically attract the guidewire.

Example 13. The apparatus of example 1 (as well as subject matter of one or more of any combination of examples 2-12, in whole or in part), wherein the guidewire holder member is at least one or more of any combination of the following: aperture, hook, loop, conduit, groove, notch, slit, lumen, bore, orifice, aperture, or channel.

Example 14. The apparatus of example 1 (as well as subject matter of one or more of any combination of examples 2-13, in whole or in part), wherein the housing comprises a housing channel to receive the retention body disposed therein to provide for the retention body being movably attached relative to the housing to allow the distal end of the retention body to advance toward the subject to a deployed position.

Example 15. The apparatus of example 14 (as well as subject matter of one or more of any combination of examples 2-13, in whole or in part), wherein the housing comprises a housing channel to receive the retention body disposed therein to provide for the retention body being movably attached relative to the housing to allow the distal end of the retention body to withdraw away from the subject to a retracted position.

Example 16. The apparatus of example 15 (as well as subject matter of one or more of any combination of examples 2-14, in whole or in part), wherein:
- the housing channel comprises a housing track disposed thereon; and
- the retention body comprises a retention body track disposed thereon, wherein the housing track and retention body track are connectably joinable with one another wherein the retention body advancement is along the joined the housing track and the retention body track.

Example 17. The apparatus of example 14 (as well as subject matter of one or more of any combination of examples 2-13 or 15-16, in whole or in part), wherein:
- the housing channel comprises a housing track disposed thereon; and
- the retention body comprises a retention body track disposed thereon, wherein the housing track and retention body track are connectably joinable with one another wherein the retention body advancement is along the joined the housing track and the retention body track.

Example 18. The apparatus of example 17 (as well as subject matter of one or more of any combination of examples 2-16, in whole or in part), wherein:
- wherein at least one check structure is disposed on the housing track defining a housing track check structure;
- wherein at least one check structure is disposed on the retention body track defining a retention body track check structure; and
- wherein the housing track check structure and the retention body track check structure are configured to contact one another during the advancement of the distal end of the retention body toward the subject to a deployed position, wherein the contact provides feedback to the user of the corresponding location of the retention body.

Example 19. The apparatus of example 18 (as well as subject matter of one or more of any combination of examples 2-17, in whole or in part), wherein the housing track check structure and/or retention body track check structure comprises one or more of any combination of the following: ridge, bump, lip, ledge, tab, notch, protrusion, groove, or indentation.

Example 20. The apparatus of example 18 (as well as subject matter of one or more of any combination of examples 2-17 or 19, in whole or in part), wherein:
the retention body comprises a wall and wherein at least one check structure is disposed on the wall of the retention body defining a retention body check structure;
the housing channel comprises a wall and wherein at least one check structure is disposed on the wall of the housing channel defining a housing channel check structure; and
wherein the retention body check structure and the housing channel check structure are configured to contact one another during the advancement of the distal end of the retention body toward the subject to a deployed position, wherein the contact provides feedback to the user of the corresponding location of the retention body.

Example 21. The apparatus of example 20 (as well as subject matter of one or more of any combination of examples 2-19, in whole or in part), wherein the housing channel check structure and/or retention body check structure comprises one or more of any combination of the following: ridge, bump, lip, ledge, tab, notch, protrusion, groove, or indentation.

Example 22. The apparatus of example 14 (as well as subject matter of one or more of any combination of examples 2-13 or 15-21, in whole or in part), wherein:
the retention body comprises a wall and wherein at least one check structure is disposed on the wall of the retention body defining a retention body check structure;
the housing channel comprises a wall and wherein at least one check structure is disposed on the wall of the housing channel defining a housing channel check structure; and
wherein the retention body check structure and the housing channel check structure are configured to contact one another during the advancement of the distal end of the retention body toward the subject to a deployed position, wherein the contact provides feedback to the user of the corresponding location of the retention body.

Example 23. The apparatus of example 22 (as well as subject matter of one or more of any combination of examples 2-21, in whole or in part), wherein the retention body check structure or housing channel check structure comprises one or more of any combination of the following: ridge, bump, lip, ledge, tab, notch, protrusion, groove, or indentation.

Example 24. The apparatus of example 14 (as well as subject matter of one or more of any combination of examples 2-13 or 15-23, in whole or in part), wherein:
the retention body comprises an upper side and wherein at least one check structure is disposed on the upper side of the retention body defining a retention body upper side check structure;
the housing comprises an under portion of an upper side and wherein at least one check structure is disposed on the under portion of the upper side of the housing defining a housing under portion-upper side check structure; and
wherein the retention body upper side check structure and the housing under portion-upper side check structure are configured to contact one another during the advancement of the distal end of the retention body toward the subject to a deployed position, wherein the contact provides feedback to the user of the corresponding location of the retention body.

Example 25. The apparatus of example 24 (as well as subject matter of one or more of any combination of examples 2-23, in whole or in part), wherein the retention body upper side check structure or housing under portion-upper side check structure comprises one or more of any combination of the following: ridge, bump, lip, ledge, tab, notch, protrusion, groove, or indentation.

Example 26. The apparatus of example 14 (as well as subject matter of one or more of any combination of examples 2-13 or 15-25, in whole or in part), wherein:
the retention body comprises an under portion of an upper side and wherein at least one check structure is disposed on the under portion of the upper side of the retention body defining a retention body under portion-upper side check structure;
the housing comprises an upper side and wherein at least one check structure is disposed on the upper side of the housing defining a housing upper side check structure; and
wherein the retention body under portion-upper side check structure and the housing upper side check structure are configured to contact one another during the advancement of the distal end of the retention body toward the subject to a deployed position, wherein the contact provides feedback to the user of the corresponding location of the retention body.

Example 27. The apparatus of example 26 (as well as subject matter of one or more of any combination of examples 2-25, in whole or in part), wherein the retention body upper side check structure or housing upper side check structure comprises one or more of any combination of the following: ridge, bump, lip, ledge, tab, notch, protrusion, groove, or indentation.

Example 28. The apparatus of example 1 (as well as subject matter of one or more of any combination of examples 2-27, in whole or in part), wherein the retention body is configured wherein the advancement of the distal end of the retention body is in substantially in the direction going from the proximal end of the retention body to the distal end of the retention body whereby the advancement direction provides for approximately about a ninety degree angle with the distal end of the housing.

Example 29. The apparatus of example 1 (as well as subject matter of one or more of any combination of examples 2-28, in whole or in part), wherein the retention body is configured wherein the advancement of the distal end of the retention body is in substantially in the direction going from the proximal end of the retention body to the distal end of the retention body whereby the advancement direction provides for an acute angle with the distal end of the housing.

Example 30. The apparatus of example 29 (as well as subject matter of one or more of any combination of examples 2-28, in whole or in part), wherein the acute angle is one of the following:

about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
    a range of about 89 to about 20 degrees.

Example 31. The apparatus of example 1 (as well as subject matter of one or more of any combination of examples 2-30, in whole or in part), wherein the retention body is configured wherein the securement of the cutting tool to the retention body provides a specified alignment of the cutting tool relative to the retention body whereby the advancement of the distal end of the retention body is in substantially in the direction going from the proximal end of the retention body to the distal end of the retention body whereby the alignment of the cutting tool provides for approximately about a ninety degree angle with the distal end of the housing.

Example 32. The apparatus of example 1 (as well as subject matter of one or more of any combination of examples 2-31, in whole or in part), wherein the retention body is configured wherein the securement of the cutting tool to the retention body provides a specified alignment of the cutting tool relative to the retention body whereby the advancement of the distal end of the retention body is in substantially in the direction going from the proximal end of the retention body to the distal end of the retention body whereby the alignment of the cutting tool provides for an acute angle with the distal end of the housing.

Example 33. The apparatus of example 32 (as well as subject matter of one or more of any combination of examples 2-31, in whole or in part), wherein the acute angle is one of the following:
    about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
    a range of about 89 to about 20 degrees.

Example 34. A surgical kit comprising:
    a cutting tool; and
    a surgical incision apparatus for puncturing a cutaneous layer of a subject for providing guided access to a subcutaneous organ or subcutaneous cavity of the subject, the apparatus comprising:
        a retention body configured for securing the cutting tool therein, wherein the retention body having a distal end and proximal end;
        a housing configured for receiving the retention body, wherein the housing having a distal end and proximal end;
        a guidewire holder member disposed on the housing configured for receiving a guidewire therein and aligning with the guidewire to allow the cutting tool to travel along the guidewire; and
        wherein the retention body is configured to be movably attached relative to the housing to allow the distal end of the retention body to advance toward the subject to a deployed position.

Example 35. The kit of example 34, wherein the retention body of the apparatus is configured to be movably attached relative to the housing to allow the distal end of the retention body to withdraw away from the subject from the deployed position to a retracted position.

Example 36. The kit of example 34 (as well as subject matter of one or more of any combination of examples 1-33, in whole or in part), further comprising the guidewire.

Example 37. A surgical method for puncturing a cutaneous layer of a subject for providing guided access to a subcutaneous organ or subcutaneous cavity of the subject, the method comprising:
    securing a cutting tool with a retention body;
    disposing the retention body with a housing;
    receiving a guidewire on the housing for aligning the housing with the guidewire; and
    advancing the retention body wherein the cutting tool travels along the guidewire and advances toward the subject to a deployed position to achieve the access to the subcutaneous organ or subcutaneous cavity of the subject.

Example 38. The method of example 37, further comprising:
    withdrawing the retention body to move the cutting tool away from the subject from the deployed position to a retracted position.

Example 39. The method of example 37 (as well as subject matter of one or more of any combination of examples 1-33, in whole or in part), further comprising:
    magnetically attracting the guidewire toward the cutting tool while the cutting tool travels along the guidewire.

Example 40. The method of example 37 (as well as subject matter of one or more of any combination of examples 1-33, in whole or in part), further comprising:
    magnetically attracting the guidewire toward a magnet disposed on the retention body and/or housing.

Example 41. The method of using any of the apparatuses (devices, structures, systems, or material) or their components or sub-components provided in any one or more of examples 1-40, in whole or in part.

Example 42. The method of using any of the apparatuses (devices, structures, systems, or material) or their components or sub-components provided in any one or more of examples 1-40, in whole or in part.

Example 43. A non-transitory machine readable medium including instructions for providing guided access to subject, which when executed by a machine, cause the machine to perform any of the steps or activities provided in any one or more of examples 37-40. Written instructions for providing guided access to subject, which when executed by a user causes the user to perform any of the steps or activities provided in any one or more of examples 37-40.

REFERENCES

The devices, systems, apparatuses, compositions, materials, machine readable medium, computer program products, and methods of various embodiments of the invention disclosed herein may utilize aspects disclosed in the following references, applications, publications and patents and which are hereby incorporated by reference herein in their entirety, and which are not admitted to be prior art with respect to the present invention by inclusion in this section:

1. U.S. Pat. No. 9,456,840 B1, Huddleston, H., "Multi-Functional Double Bladed Surgical Tool", Oct. 4, 2016.
2. U.S. Pat. No. 8,795,384 B2, Nelson, et al., "Implantable Devices Useful for Reinforcing a Surgically Created Stoma", Aug. 5, 2014.
3. U.S. Pat. No. 8,752,700 B1, Hoftman, M., "Sharps Container with Blade Remover, Needle Unsheather, Latch and Security Alignment Extensions", Jun. 17, 2014.
4. U.S. Pat. No. 8,596,453 A0, Hoftman, et al., "Scalpel Blade Remover and Sharps Container", Dec. 3, 2013.
5. U.S. Pat. No. 8,512,363 B2, Heppler, J., "Channeled Wire Guide for a Scalpel", Aug. 20, 2013.

6. U.S. Pat. No. 8,172,801 B2, Adams, M., "Method for Positioning a Catheter Guide Element in a Patient and Kit for use in said Method", May 8, 2012.
7. U.S. Pat. No. 7,341,596 B2, Heppler, J., "Wire Guides for a Scalpel", Mar. 11, 2008.
8. U.S. Pat. No. 7,172,611 B2, Harding, et al., "Surgical Scalpel Assembly", Feb. 6, 2007.
9. U.S. Pat. No. 6,663,616 B1, Roth, et al., "Set of Surgical Instruments", Dec. 16, 2003.
10. U.S. Pat. No. 6,270,501 B1, Freiberg, et al., "Surgical Method and Apparatus and Cannulated Scalpel for use therein", Aug. 7, 2001.
11. U.S. Pat. No. 5,868,250, Brackett, F., "Tray for Holding Medical Instruments", Feb. 9, 1999.
12. U.S. Pat. No. 5,817,117, Cartaxo, S., "Surgical Instrument in the Form of a Scalpel and Guide for Making Perfectly Circular Incisions", Oct. 6, 1998.
13. U.S. Pat. No. 5,749,886, Abidin, et al., "Disposable Guarded Finger Scalpel for Inserting a Line in a Patient and Blade Therefor", May 12, 1998.
14. U.S. Pat. No. 5,649,944, Collins, J., "Apparatus for Preparing Cornea Material for Tabbed (Sutureless) Transplantation", Jul. 22, 1997.
15. U.S. Pat. No. 5,449,068, Gharibian, N., "Surgical Blade Remover", Sep. 12, 1995.
16. U.S. Pat. No. 5,108,408, Lally, J., "Uterine-Ring Hysterectomy Clamp", Apr. 28, 1992.
17. U.S. Pat. No. 4,730,376, Yamada, K., "Blade Removal Apparatus for Changeable Blade Scalpel", Mar. 18, 1988.
18. U.S. Pat. No. 4,688,570, Kramer, et al., "Ophthalmological Surgical Instrument", Aug. 25, 1987.
19. U.S. Pat. No. 4,655,223, Kim, D., "Frenotomy Method and Apparatus", Apr. 7, 1987.
20. U.S. Pat. No. 4,633,860, Korth, et al., "Canal Forming Device for Percutaneous Nephroscopy", Jan. 6, 1987.
21. U.S. Pat. No. 4,517,973, Sunago, et al., "Laser Scalpel", May 21, 1985.
22. U.S. Pat. No. 4,378,624, Klingenberg, R., "Scalpel Blade Remover", Apr. 5, 1983.
23. U.S. Pat. No. 4,270,416, Thompson, D., "Scalpel Blade Extraction", Jun. 2, 1981.
24. U.S. Pat. No. 4,266,549, Kimura, H., "Laser Scalpel", May 12, 1981.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A surgical method for puncturing a cutaneous layer of a subject for providing guided access to a subcutaneous organ or subcutaneous cavity of the subject, said method comprising:
    securing a cutting tool with a retention body;
    disposing said retention body within a housing;
    receiving a guidewire on said housing for aligning said housing with said guidewire;
    advancing said retention body wherein said cutting tool travels along said guidewire and advances toward the subject to a deployed position to achieve said access to the subcutaneous organ or subcutaneous cavity of the subject; and
    magnetically attracting said guidewire toward said cutting tool while said cutting tool travels along said guidewire.

2. The method of claim 1, further comprising:
    withdrawing said retention body to move said cutting tool away from the subject from said deployed position to a retracted position.

3. A surgical method for puncturing a cutaneous layer of a subject for providing guided access to a subcutaneous organ or subcutaneous cavity of the subject, said method comprising:
   securing a cutting tool with a retention body;
   disposing said retention body within a housing;
   receiving a guidewire on said housing for aligning said housing with said guidewire;
   advancing said retention body wherein said cutting tool travels along said guidewire and advances toward the subject to a deployed position to achieve said access to the subcutaneous organ or subcutaneous cavity of the subject; and
   magnetically attracting said guidewire toward a magnet disposed on said retention body and/or housing.

4. The method of claim 3, further comprising:
   withdrawing said retention body to move said cutting tool away from the subject from said deployed position to a retracted position.

5. A surgical incision apparatus for puncturing a cutaneous layer of a subject for providing guided access to a subcutaneous organ or subcutaneous cavity of the subject, said apparatus comprising:
   a retention body configured for securing a cutting tool therein, wherein said retention body having a distal end and proximal end;
   a housing configured for receiving said retention body, wherein said housing having a distal end and proximal end;
   a guidewire holder member disposed on said housing configured for receiving a guidewire therein and aligning with said guidewire to allow said cutting tool to travel along said guidewire;
   wherein said retention body is configured to be movably attached relative to said housing to allow said distal end of said retention body to advance toward the subject to a deployed position; and
   at least one magnet disposed on said housing, wherein said magnet having a distal end and proximal end, and wherein said magnet is configured to magnetize said cutting tool whereby said magnetization of said cutting tool magnetically attracts said guidewire.

6. The apparatus of claim 5, wherein said retention body is configured to be movably attached relative to said housing to allow said distal end of said retention body to withdraw away from the subject from said deployed position to a retracted position.

7. The apparatus of claim 5, further comprising said cutting tool provided together in a kit with said apparatus.

8. The apparatus of claim 5, wherein said cutting tool is at least one or more of any combination of the following: scalpel, bowie, knife, blade, or other cutting instrument.

9. The apparatus of claim 5, further comprising said guidewire provided together in a kit with said apparatus.

10. The apparatus of claim 5, further comprising at least one repository disposed in said housing, wherein said repository is configured contain at least one said magnet in said repository.

11. The apparatus of claim 5, wherein said at least one magnet is configured to magnetically attract said guidewire.

12. The apparatus of claim 5, wherein said guidewire holder member is at least one or more of any combination of the following: aperture, hook, loop, conduit, groove, notch, slit, lumen, bore, orifice, aperture, or channel.

13. The apparatus of claim 5, wherein said housing comprises a housing channel to receive said retention body disposed therein to provide for said retention body being movably attached relative to said housing to allow said distal end of said retention body to advance toward the subject to a deployed position.

14. The apparatus of claim 13, wherein said housing comprises a housing channel to receive said retention body disposed therein to provide for said retention body being movably attached relative to said housing to allow said distal end of said retention body to withdraw away from the subject to a retracted position.

15. The apparatus of claim 14, wherein:
   said housing channel comprises a housing track disposed thereon; and
   said retention body comprises a retention body track disposed thereon, wherein said housing track and retention body track are connectably joinable with one another wherein said retention body advancement is along said joined said housing track and said retention body track.

16. The apparatus of claim 13, wherein:
   said housing channel comprises a housing track disposed thereon; and
   said retention body comprises a retention body track disposed thereon, wherein said housing track and retention body track are connectably joinable with one another wherein said retention body advancement is along said joined said housing track and said retention body track.

17. The apparatus of claim 16, wherein:
   wherein at least one check structure is disposed on said housing track defining a housing track check structure;
   wherein at least one check structure is disposed on said retention body track defining a retention body track check structure; and
   wherein said housing track check structure and said retention body track check structure are configured to contact one another during said advancement of said distal end of said retention body toward the subject to a deployed position, wherein said contact provides feedback to the user of the corresponding location of the retention body.

18. The apparatus of claim 17, wherein said housing track check structure and/or retention body track check structure comprises one or more of any combination of the following: ridge, bump, lip, ledge, tab, notch, protrusion, groove, or indentation.

19. The apparatus of claim 17, wherein:
   said retention body comprises a wall and wherein at least one check structure is disposed on said wall of said retention body defining a retention body check structure;
   said housing channel comprises a wall and wherein at least one check structure is disposed on said wall of said housing channel defining a housing channel check structure; and
   wherein said retention body check structure and said housing channel check structure are configured to contact one another during said advancement of said distal end of said retention body toward the subject to a deployed position, wherein said contact provides feedback to the user of the corresponding location of the retention body.

20. The apparatus of claim 19, wherein said housing channel check structure and/or retention body check structure comprises one or more of any combination of the following: ridge, bump, lip, ledge, tab, notch, protrusion, groove, or indentation.

21. The apparatus of claim 13, wherein:
said retention body comprises a wall and wherein at least one check structure is disposed on said wall of said retention body defining a retention body check structure;
said housing channel comprises a wall and wherein at least one check structure is disposed on said wall of said housing channel defining a housing channel check structure; and
wherein said retention body check structure and said housing channel check structure are configured to contact one another during said advancement of said distal end of said retention body toward the subject to a deployed position, wherein said contact provides feedback to the user of the corresponding location of the retention body.

22. The apparatus of claim 21, wherein said retention body check structure or housing channel check structure comprises one or more of any combination of the following: ridge, bump, lip, ledge, tab, notch, protrusion, groove, or indentation.

23. The apparatus of claim 13, wherein:
said retention body comprises an upper side and wherein at least one check structure is disposed on said upper side of said retention body defining a retention body upper side check structure;
said housing comprises an under portion of an upper side and wherein at least one check structure is disposed on said under portion of said upper side of said housing defining a housing under portion-upper side check structure; and
wherein said retention body upper side check structure and said housing under portion-upper side check structure are configured to contact one another during said advancement of said distal end of said retention body toward the subject to a deployed position, wherein said contact provides feedback to the user of the corresponding location of the retention body.

24. The apparatus of claim 23, wherein said retention body upper side check structure or housing under portion-upper side check structure comprises one or more of any combination of the following: ridge, bump, lip, ledge, tab, notch, protrusion, groove, or indentation.

25. The apparatus of claim 13, wherein:
said retention body comprises an under portion of an upper side and wherein at least one check structure is disposed on said under portion of said upper side of said retention body defining a retention body under portion-upper side check structure;
said housing comprises an upper side and wherein at least one check structure is disposed on said upper side of said housing defining a housing upper side check structure; and
wherein said retention body under portion-upper side check structure and said housing upper side check structure are configured to contact one another during said advancement of said distal end of said retention body toward the subject to a deployed position, wherein said contact provides feedback to the user of the corresponding location of the retention body.

26. The apparatus of claim 25, wherein said retention body upper side check structure or housing upper side check structure comprises one or more of any combination of the following: ridge, bump, lip, ledge, tab, notch, protrusion, groove, or indentation.

27. The apparatus of claim 5, wherein said retention body is configured wherein said advancement of said distal end of said retention body is in substantially in the direction going from the proximal end of the retention body to the distal end of the retention body whereby the advancement direction provides for approximately about a ninety degree angle with the distal end of the housing.

28. The apparatus of claim 5, wherein said retention body is configured wherein said advancement of said distal end of said retention body is in substantially in the direction going from the proximal end of the retention body to the distal end of the retention body whereby the advancement direction provides for an acute angle with the distal end of the housing.

29. The apparatus of claim 28, wherein said acute angle is one of the following:
about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
a range of about 89 to about 20 degrees.

30. The apparatus of claim 5, wherein said retention body is configured wherein said securement of said cutting tool to said retention body provides a specified alignment of said cutting tool relative to said retention body whereby said advancement of said distal end of said retention body is in substantially in the direction going from the proximal end of the retention body to the distal end of the retention body whereby the alignment of said cutting tool provides for approximately about a ninety degree angle with the distal end of the housing.

31. The apparatus of claim 5, wherein said retention body is configured wherein said securement of said cutting tool to said retention body provides a specified alignment of said cutting tool relative to said retention body whereby said advancement of said distal end of said retention body is in substantially in the direction going from the proximal end of the retention body to the distal end of the retention body whereby the alignment of said cutting tool provides for an acute angle with the distal end of the housing.

32. The apparatus of claim 31, wherein said acute angle is one of the following:
about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
a range of about 89 to about 20 degrees.

33. A surgical incision apparatus for puncturing a cutaneous layer of a subject for providing guided access to a subcutaneous organ or subcutaneous cavity of the subject, said apparatus comprising:
a retention body configured for securing a cutting tool therein, wherein said retention body having a distal end and proximal end;
a housing configured for receiving said retention body, wherein said housing having a distal end and proximal end;
a guidewire holder member disposed on said housing configured for receiving a guidewire therein and aligning with said guidewire to allow said cutting tool to travel along said guidewire;
wherein said retention body is configured to be movably attached relative to said housing to allow said distal end of said retention body to advance toward the subject to a deployed position; and
at least one magnet disposed on said housing, wherein said magnet having a distal end and proximal end, and wherein said magnet is configured to magnetically attract said guidewire.

34. The apparatus of claim 33, wherein said retention body is configured to be movably attached relative to said housing to allow said distal end of said retention body to withdraw away from the subject from said deployed position to a retracted position.

35. The apparatus of claim 33, further comprising said cutting tool provided together in a kit with said apparatus.

36. The apparatus of claim 33, wherein said cutting tool is at least one or more of any combination of the following: scalpel, Bovie, knife, blade, or other cutting instrument.

37. The apparatus of claim 33, further comprising said guidewire provided together in a kit with said apparatus.

38. The apparatus of claim 33, wherein said guidewire holder member is at least one or more of any combination of the following: aperture, hook, loop, conduit, groove, notch, slit, lumen, bore, orifice, aperture, or channel.

39. The apparatus of claim 33, wherein said housing comprises a housing channel to receive said retention body disposed therein to provide for said retention body being movably attached relative to said housing to allow said distal end of said retention body to advance toward the subject to a deployed position.

40. The apparatus of claim 39, wherein said housing comprises a housing channel to receive said retention body disposed therein to provide for said retention body being movably attached relative to said housing to allow said distal end of said retention body to withdraw away from the subject to a retracted position.

41. The apparatus of claim 40, wherein:
said housing channel comprises a housing track disposed thereon; and
said retention body comprises a retention body track disposed thereon, wherein said housing track and retention body track are connectably joinable with one another wherein said retention body advancement is along said joined said housing track and said retention body track.

42. The apparatus of claim 39, wherein:
said housing channel comprises a housing track disposed thereon; and
said retention body comprises a retention body track disposed thereon, wherein said housing track and retention body track are connectably joinable with one another wherein said retention body advancement is along said joined said housing track and said retention body track.

43. The apparatus of claim 42, wherein:
wherein at least one check structure is disposed on said housing track defining a housing track check structure;
wherein at least one check structure is disposed on said retention body track defining a retention body track check structure; and
wherein said housing track check structure and said retention body track check structure are configured to contact one another during said advancement of said distal end of said retention body toward the subject to a deployed position, wherein said contact provides feedback to the user of the corresponding location of the retention body.

44. The apparatus of claim 43, wherein said housing track check structure and/or retention body track check structure comprises one or more of any combination of the following: ridge, bump, lip, ledge, tab, notch, protrusion, groove, or indentation.

45. The apparatus of claim 43, wherein:
said retention body comprises a wall and wherein at least one check structure is disposed on said wall of said retention body defining a retention body check structure;
said housing channel comprises a wall and wherein at least one check structure is disposed on said wall of said housing channel defining a housing channel check structure; and
wherein said retention body check structure and said housing channel check structure are configured to contact one another during said advancement of said distal end of said retention body toward the subject to a deployed position, wherein said contact provides feedback to the user of the corresponding location of the retention body.

46. The apparatus of claim 45, wherein said housing channel check structure and/or retention body check structure comprises one or more of any combination of the following: ridge, bump, lip, ledge, tab, notch, protrusion, groove, or indentation.

47. The apparatus of claim 39, wherein:
said retention body comprises a wall and wherein at least one check structure is disposed on said wall of said retention body defining a retention body check structure;
said housing channel comprises a wall and wherein at least one check structure is disposed on said wall of said housing channel defining a housing channel check structure; and
wherein said retention body check structure and said housing channel check structure are configured to contact one another during said advancement of said distal end of said retention body toward the subject to a deployed position, wherein said contact provides feedback to the user of the corresponding location of the retention body.

48. The apparatus of claim 47, wherein said retention body check structure or housing channel check structure comprises one or more of any combination of the following: ridge, bump, lip, ledge, tab, notch, protrusion, groove, or indentation.

49. The apparatus of claim 39, wherein:
said retention body comprises an upper side and wherein at least one check structure is disposed on said upper side of said retention body defining a retention body upper side check structure;
said housing comprises an under portion of an upper side and wherein at least one check structure is disposed on said under portion of said upper side of said housing defining a housing under portion-upper side check structure; and
wherein said retention body upper side check structure and said housing under portion-upper side check structure are configured to contact one another during said advancement of said distal end of said retention body toward the subject to a deployed position, wherein said contact provides feedback to the user of the corresponding location of the retention body.

50. The apparatus of claim 49, wherein said retention body upper side check structure or housing under portion-upper side check structure comprises one or more of any combination of the following: ridge, bump, lip, ledge, tab, notch, protrusion, groove, or indentation.

51. The apparatus of claim 39, wherein:
said retention body comprises an under portion of an upper side and wherein at least one check structure is disposed on said under portion of said upper side of said retention body defining a retention body under portion-upper side check structure;

said housing comprises an upper side and wherein at least one check structure is disposed on said upper side of said housing defining a housing upper side check structure; and wherein said retention body under portion-upper side check structure and said housing upper side check structure are configured to contact one another during said advancement of said distal end of said retention body toward the subject to a deployed, position, wherein said contact provides feedback to the user of the corresponding location of the retention body.

52. The apparatus of claim 51, wherein said retention body upper side check structure or housing upper side check structure comprises one or more of any combination of the following: ridge, bump, lip, ledge, tab, notch, protrusion, groove, or indentation.

53. The apparatus of claim 33, wherein said retention body is configured wherein said advancement of said distal end of said retention body is in substantially in the direction going from the proximal end of the retention body to the distal end of the retention body whereby the advancement direction provides for approximately about a ninety degree angle with the distal end of the housing.

54. The apparatus of claim 33, wherein said retention body is configured wherein said advancement of said distal end of said retention body is in substantially in the direction going from the proximal end of the retention body to the distal end of the retention body whereby the advancement direction provides for an acute angle with the distal end of the housing.

55. The apparatus of claim 54, wherein said acute angle is one of the following:
about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
a range of about 89 to about 20 degrees.

56. The apparatus of claim 33, wherein said retention body is configured wherein said securement of said cutting tool to said retention body provides a specified alignment of said cutting tool relative to said retention body whereby said advancement of said distal end of said retention body is in substantially in the direction going from the proximal end of the retention body to the distal end of the retention body whereby the alignment of said cutting tool provides for approximately about a ninety degree angle with the distal end of the housing.

57. The apparatus of claim 33, wherein said retention body is configured wherein said securement of said cutting tool to said retention body provides a specified alignment of said cutting tool relative to said retention body whereby said advancement of said distal end of said retention body is in substantially in the direction going from the proximal end of the retention body to the distal end of the retention body whereby the alignment of said cutting tool provides for an acute angle with the distal end of the housing.

58. The apparatus of claim 57, wherein said acute angle is one of the following:
about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
a range of about 89 to about 20 degrees.

59. A surgical incision apparatus for puncturing a cutaneous layer of a subject for providing guided access to a subcutaneous organ or subcutaneous cavity of the subject, said apparatus comprising:
a retention body configured for securing a cutting tool therein, wherein said retention body having a distal end and proximal end;
a housing configured for receiving said retention body, wherein said housing having a distal end and proximal end;
a guidewire holder member disposed on said housing configured for receiving a guidewire therein and aligning with said guidewire to allow said cutting tool to travel along said guidewire;
wherein said retention body is configured to be movably attached relative to said housing to allow said distal end of said retention body to advance toward the subject to a deployed position; and
at least one magnet disposed on said retention body, wherein said magnet having a distal end and proximal end, and wherein said magnet is configured to magnetize said cutting tool whereby said magnetization of said cutting tool magnetically attracts said guidewire.

60. The apparatus of claim 59, wherein said retention body is configured to be movably attached relative to said housing to allow said distal end of said retention body to withdraw away from the subject from said deployed position to a retracted position.

61. The apparatus of claim 59, further comprising said cutting tool provided together in a kit with said apparatus.

62. The apparatus of claim 59, wherein said cutting tool is at feast one or more of any combination of the following: scalpel, bowie, knife, blade, or other cutting instrument.

63. The apparatus of claim 59, further comprising said guidewire provided together in a kit with said apparatus.

64. The apparatus of claim 53, wherein said at least one magnet is configured to magnetically attract said guidewire.

65. The apparatus of claim 59, wherein said guidewire holder member is at least one or more of any combination of the following: aperture, hook, loop, conduit, groove, notch, slit, lumen, bore, orifice, aperture, or channel.

66. The apparatus of claim 59, wherein said housing comprises a housing channel to receive said retention body disposed therein to provide for said retention body being movably attached relative to said housing to allow said distal end of said retention body to advance toward the subject to a deployed position.

67. The apparatus of claim 66, wherein said housing comprises a housing channel to receive said retention body disposed therein to provide for said retention body being movably attached relative to said housing to allow said distal end of said retention body to withdraw away from the subject to a retracted position.

68. The apparatus of claim 67, wherein:
said housing channel comprises a housing track disposed thereon; and
said retention body comprises a retention body track disposed thereon, wherein said housing track and retention body track are connectably joinable with one another wherein said retention body advancement is along said joined said housing track and said retention body track.

69. The apparatus of claim 66, wherein:
said housing channel comprises a housing track disposed thereon; and
said retention body comprises a retention body track disposed thereon, wherein said housing track and retention body track are connectably joinable with one another wherein said retention body advancement is along said joined said housing track and said retention body track.

70. The apparatus of claim 69, wherein:
wherein at least one check structure is disposed on said housing track defining a housing track check structure;
wherein at least one check structure is disposed on said retention body track defining a retention body track check structure; and
wherein said housing track check structure and said retention body track check structure are configured to contact one another during said advancement of said distal end of said retention body toward the subject to a deployed position, wherein said contact provides feedback to the user of the corresponding location of the retention body.

71. The apparatus of claim 70, wherein said housing track check structure and/or retention body track check structure comprises one or more of any combination of the following: ridge, bump, lip, ledge, tab, notch, protrusion, groove, or indentation.

72. The apparatus of claim 70, wherein:
said retention body comprises a wall and wherein at least one check structure is disposed on said wall of said retention body defining a retention body check structure;
said housing channel comprises a wall and wherein at least one check structure is disposed on said wall of said housing channel defining a housing channel check structure; and
wherein said retention body check structure and said housing channel check structure are configured to contact one another during said advancement of said distal end of said retention body toward the subject to a deployed position, wherein said contact provides feedback to the user of the corresponding location of the retention body.

73. The apparatus of claim 72, wherein said housing channel check structure and/or retention body check structure comprises one or more of any combination of the following: ridge, bump, lip, ledge, tab, notch, protrusion, groove, or indentation.

74. The apparatus of claim 66, wherein:
said retention body comprises a wall and wherein at least one check structure is disposed on said wall of said retention body defining a retention body check structure;
said housing channel comprises a wall and wherein at least one check structure is disposed on said wall of said housing channel defining a housing channel check structure; and
wherein said retention body check structure and said housing channel check structure are configured to contact one another during said advancement of said distal end of said retention body toward the subject to a deployed position, wherein said contact provides feedback to the user of the corresponding location of the retention body.

75. The apparatus of claim 74, wherein said retention body check structure or housing channel check structure comprises one or more of any combination of the following: ridge, bump, lip, ledge, tab, notch, protrusion, groove, or indentation.

76. The apparatus of claim 66, wherein:
said retention body comprises an upper side and wherein at least one check structure is disposed on said upper side of said retention body defining a retention body upper side check structure;
said housing comprises an under portion of an upper side and wherein at least one check structure is disposed on said under portion of said upper side of said housing defining a housing under portion-upper side check structure; and
wherein said retention body upper side check structure and said housing under portion-upper side check structure are configured to contact one another during said advancement of said distal end of said retention body toward the subject to a deployed position, wherein said contact provides feedback to the user of the corresponding location of the retention body.

77. The apparatus of claim 76, wherein said retention body upper side check structure or housing under portion-upper side check structure comprises one or more of any combination of the following: ridge, bump, lip, ledge, tab, notch, protrusion, groove, or indentation.

78. The apparatus of claim 66, wherein:
said retention body comprises an under portion of an upper side and wherein at least one check structure is disposed on said under portion of said upper side of said retention body defining a retention body under portion-upper side check structure;
said housing comprises an upper side and wherein at least one check structure is disposed on said upper side of said housing defining a housing upper side check structure; and
wherein said retention body under portion-upper side check structure and said housing upper side check structure are configured to contact one another during said advancement of said distal end of said retention body toward the subject to a deployed position, wherein said contact provides feedback to the user of the corresponding location of the retention body.

79. The apparatus of claim 78, wherein said retention body upper side check structure or housing upper side check structure comprises one or more of any combination of the following: ridge, bump, lip, ledge, tab, notch, protrusion, groove, or indentation.

80. The apparatus of claim 59, wherein said retention body is configured wherein said advancement of said distal end of said retention body is in substantially in the direction going from the proximal end of the retention body to the distal end of the retention body whereby the advancement direction provides for approximately about a ninety degree angle with the distal end of the housing.

81. The apparatus of claim 59, wherein said retention body is configured wherein said advancement of said distal end of said retention body is in substantially in the direction going from the proximal end of the retention body to the distal end of the retention body whereby the advancement direction provides for an acute angle with the distal end of the housing.

82. The apparatus of claim 81, wherein said acute angle is one of the following:
about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
a range of about 89 to about 20 degrees.

83. The apparatus of claim 59, wherein said retention body is configured wherein said securement of said cutting tool to said retention body provides a specified alignment of said cutting tool relative to said retention body whereby said advancement of said distal end of said retention body is in substantially in the direction going from the proximal end of the retention body to the distal end of the retention body whereby the alignment of said cutting tool provides for approximately about a ninety degree angle with the distal end of the housing.

84. The apparatus of claim 59, wherein said retention body is configured wherein said securement of said cutting tool to said retention body provides a specified alignment of said cutting tool relative to said retention body whereby said advancement of said distal end of said retention body is in substantially in the direction going from the proximal end of the retention body to the distal end of the retention body whereby the alignment of said cutting tool provides for an acute angle with the distal end of the housing.

85. The apparatus of claim 84, wherein said acute angle is one of the following:
about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
a range of about 89 to about 20 degrees.

86. A surgical incision apparatus for puncturing a cutaneous layer of a subject for providing guided access to a subcutaneous organ or subcutaneous cavity of the subject, said apparatus comprising:
a retention body configured for securing a cutting tool therein, wherein said retention body having a distal end and proximal end;
a housing configured for receiving said retention body, wherein said housing having a distal end and proximal end;
a guidewire holder member disposed on said housing configured for receiving a guidewire therein and aligning with said guidewire to allow said cutting tool to travel along said guidewire;
wherein said retention body is configured to be movably attached relative to said housing to allow said distal end of said retention body to advance toward the subject to a deployed position; and
at least one magnet disposed on said retention body, wherein said magnet having a distal end and proximal end, and wherein said magnet is configured to magnetically attract said guidewire.

87. The apparatus of claim 86, wherein said retention body is configured to be movably attached relative to said housing to allow said distal end of said retention body to withdraw away from the subject from said deployed position to a retracted position.

88. The apparatus of claim 86, further comprising said cutting tool provided together in a kit with said apparatus.

89. The apparatus of claim 86, wherein said cutting tool is at least one or more of any combination of the following: scalpel, bovie, knife, blade, or other cutting instrument.

90. The apparatus of claim 86, further comprising said guidewire provided together in a kit with said apparatus.

91. The apparatus of claim 86, wherein said guidewire holder member is at least one or more of any combination of the following: aperture, hook, loop, conduit, groove, notch, slit, lumen, bore, orifice, aperture, or channel.

92. The apparatus of claim 86, wherein said housing comprises a housing channel to receive said retention body disposed therein to provide for said retention body being movably attached relative to said housing to allow said distal end of said retention body to advance toward the subject to a deployed position.

93. The apparatus of claim 92, wherein said housing comprises a housing channel to receive said retention body disposed therein to provide for said retention body being movably attached relative to said housing to allow said distal end of said retention body to withdraw away from the subject to a retracted position.

94. The apparatus of claim 93, wherein:
said housing channel comprises a housing track disposed thereon; and
said retention body comprises a retention body track disposed thereon, wherein said housing track and retention body track are connectably joinable with one another wherein said retention body advancement is along said joined said housing track and said retention body track.

95. The apparatus of claim 92, wherein:
said housing channel comprises a housing track disposed thereon; and
said retention body comprises a retention body track disposed thereon, wherein said housing track and retention body track are connectably joinable with one another wherein said retention body advancement is along said joined said housing track and said retention body track.

96. The apparatus of claim 95, wherein:
wherein at least one check structure is disposed on said housing track defining a housing track check structure;
wherein at least one check structure is disposed on said retention body track defining a retention body track check structure; and
wherein said housing track check structure and said retention body track check structure are configured to contact one another during said advancement of said distal end of said retention body toward the subject to a deployed position, wherein said contact provides feedback to the user of the corresponding location of the retention body.

97. The apparatus of claim 96, wherein said housing track check structure and/or retention body track check structure comprises one or more of any, combination of the following: ridge, bump, lip, ledge, tab, notch, protrusion, groove, or indentation.

98. The apparatus of claim 96, wherein:
said retention body comprises a wall and wherein at least one check structure is disposed on said wall of said retention body defining a retention body check structure;
said housing channel comprises a wall and wherein at least one check structure is disposed on said wall of said housing channel defining a housing channel check structure; and
wherein said retention body check structure and said housing channel check structure are configured to contact one another during said advancement of said distal end of said retention body toward the subject to a deployed position, wherein said contact provides feedback to the user of the corresponding location of the retention body.

99. The apparatus of claim 98, wherein said housing channel check structure and/or retention body check structure comprises one or more of any combination of the following: ridge, hump, lip, ledge, tab, notch, protrusion, groove, or indentation.

100. The apparatus of claim 92, wherein:
said retention body comprises a wall and wherein at least one check structure is disposed on said wall of said retention body defining a retention body check structure;

said housing channel comprises a wall and wherein at least one check structure is disposed on said wall of said housing channel defining a housing channel check structure; and wherein said retention body check structure and said housing channel check structure are configured to contact one another during said advancement of said distal end of said retention body toward the subject to a deployed position, wherein said contact provides feedback to the user of the corresponding location of the retention body.

101. The apparatus of claim 100, wherein said retention body check structure or housing channel check structure comprises one or more of any combination of the following: ridge, bump, lip, ledge, tab, notch, protrusion, groove, or indentation.

102. The apparatus of claim 92, wherein:
said retention body comprises an upper side and wherein at least one check structure is disposed on said upper side of said retention body defining a retention body upper side check structure;
said housing comprises an under portion of an upper side and wherein at least one check structure is disposed on said under portion of said upper side of said housing defining a housing under portion-upper side check structure; and
wherein said retention body upper side check structure and said housing under portion-upper side check structure are configured to contact one another during said advancement of said distal end of said retention body toward the subject to a deployed position, wherein said contact provides feedback to the user of the corresponding location of the retention body.

103. The apparatus of claim 102, wherein said retention body upper side check structure or housing under portion-upper side check structure comprises one or more of any combination of the following: ridge, bump, lip, ledge, tab, notch, protrusion, groove, or indentation.

104. The apparatus of claim 92, wherein:
said retention body comprises an under portion of an upper side and wherein at least one check structure is disposed on said under portion of said upper side of said retention body defining a retention body under portion-upper side check structure;
said housing comprises an upper side and wherein at least one check structure is disposed on said upper side of said housing defining a housing upper side check structure; and
wherein said retention body under portion-upper side check structure and said housing upper side check structure are configured to contact one another during said advancement of said distal end of said retention body toward the subject to a deployed position, wherein said contact provides feedback to the user of the corresponding location of the retention body.

105. The apparatus of claim 104, wherein said retention body upper side check structure or housing upper side check structure comprises one or more of any combination of the following: ridge, bump, lip, ledge, tab, notch, protrusion, groove, or indentation.

106. The apparatus of claim 86, wherein said retention body is configured wherein said advancement of said distal end of said retention body is in substantially in the direction going from the proximal end of the retention body to the distal end of the retention body whereby the advancement direction provides for approximately about a ninety degree angle with the distal end of the housing.

107. The apparatus of claim 86, wherein said retention body is configured wherein said advancement of said distal end of said retention body is in substantially in the direction going from the proximal end of the retention body to the distal end of the retention body whereby the advancement direction provides for an acute angle with the distal end of the housing.

108. The apparatus of claim 107, wherein said acute angle is one of the following:
about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
a range of about 89 to about 20 degrees.

109. The apparatus of claim 86, wherein said retention body is configured wherein said securement of said cutting tool to said retention body provides a specified alignment of said cutting tool relative to said retention body whereby said advancement of said distal end of said retention body is in substantially in the direction going from the proximal end of the retention body to the distal end of the retention body whereby the alignment of said cutting tool provides for approximately about a ninety degree angle with the distal end of the housing.

110. The apparatus of claim 86, wherein said retention body is configured wherein said securement of said cutting tool to said retention body provides a specified alignment of said cutting tool relative to said retention body whereby said advancement of said distal end of said retention body is in substantially in the direction going from the proximal end of the retention body to the distal end of the retention body whereby the alignment of said cutting tool provides for an acute angle with the distal end of the housing.

111. The apparatus of claim 110, wherein said acute angle is one of the following:
about 85 degrees, about 80 degrees, about 75 degrees, about 70 degrees, about 65 degrees, about 55 degrees, about 50 degrees, about 45 degrees, about 40 degrees, about 35 degrees, or about 30 degrees; or
a range of about 89 to about 20 degrees.

* * * * *